(12) United States Patent
Tobimatsu

(10) Patent No.: US 7,355,194 B2
(45) Date of Patent: Apr. 8, 2008

(54) OPTICAL DEVICE AND TURBIDITY DETECTION APPARATUS USING SAME

(75) Inventor: Hiroaki Tobimatsu, Kobe (JP)

(73) Assignee: Sysmex Corporation, Kobe (JP)

( * ) Notice: Subject to any disclaimer, the term of this patent is extended or adjusted under 35 U.S.C. 154(b) by 3 days.

(21) Appl. No.: 11/040,980

(22) Filed: Jan. 21, 2005

(65) Prior Publication Data

US 2005/0156124 A1 Jul. 21, 2005

(30) Foreign Application Priority Data

Jan. 21, 2004 (JP) .............................. 2004-013519

(51) Int. Cl.
*G01N 15/06* (2006.01)
*G01N 21/00* (2006.01)
*G08B 21/00* (2006.01)

(52) U.S. Cl. .................. 250/573; 250/576; 356/436; 340/603

(58) Field of Classification Search ............... 250/573, 250/575, 576, 577; 356/436, 441, 442, 437, 356/440; 340/602, 619, 603; 73/61.48, 73/61.59, 61.69, 64.43, 64.56, 64.55
See application file for complete search history.

(56) References Cited

U.S. PATENT DOCUMENTS 3,864,044 A * 2/1975 Lyshkow .................... 356/436

6,410,278 B1 6/2002 Notomi et al.
6,844,934 B2 * 1/2005 Retzlaff et al. ............. 356/436

FOREIGN PATENT DOCUMENTS

JP H05-133893 5/1993

* cited by examiner

*Primary Examiner*—Georgia Epps
*Assistant Examiner*—Don Williams
(74) *Attorney, Agent, or Firm*—Brinks Hofer Gilson & Lione

(57) ABSTRACT

An optical device is described that include: a photoemitter for emitting light, a mounting unit for installing a transparent container accommodating a sample to be subjected to detection, a photoreceptor for receiving the light emitted by a photoemitter and transmitted through the transparent container installed in the mounting unit, a first member disposed between the transparent container and the photoreceptor and having a first pinhole through which passes the light transmitted through the transparent container, and a second member disposed between the first member and the photoreceptor and having a second pinhole through which passes the transmitted light that has passed through the first pinhole.

20 Claims, 17 Drawing Sheets

[Fig. 1]
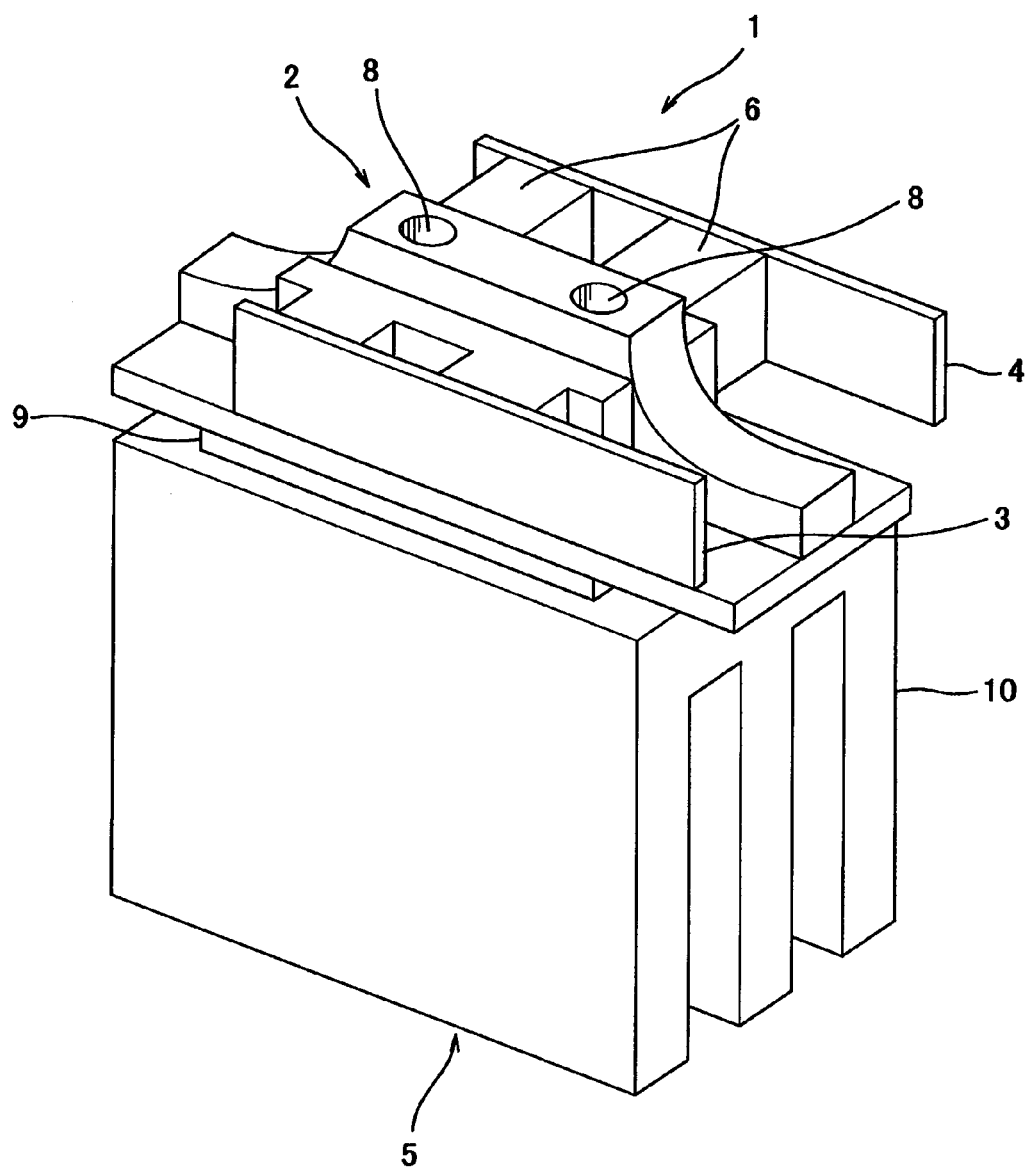

[Fig. 2]
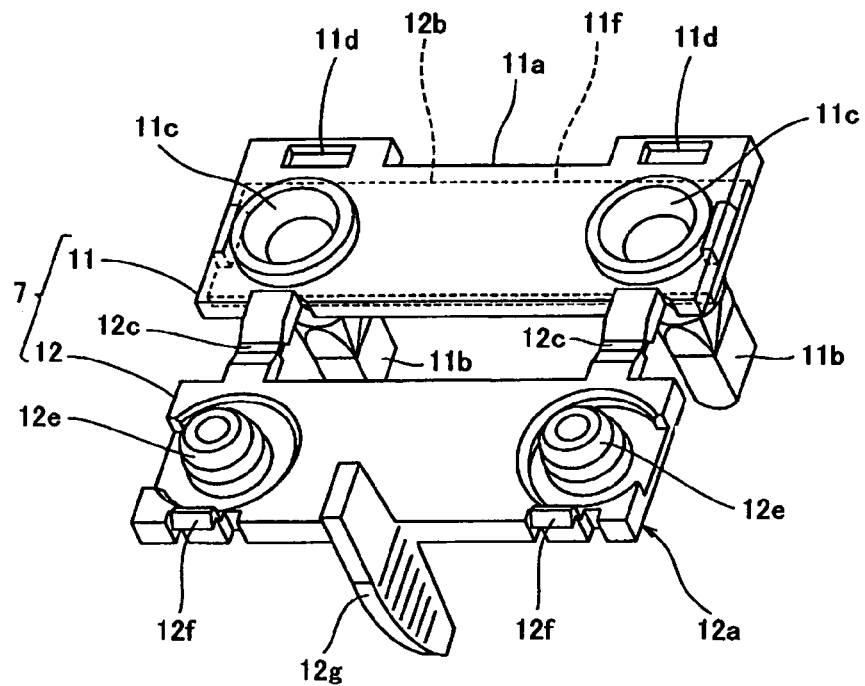
[Fig. 3]
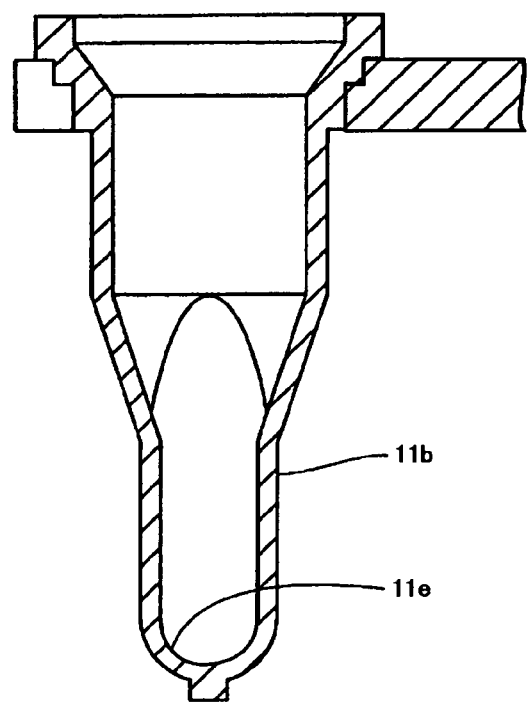

[Fig. 4]
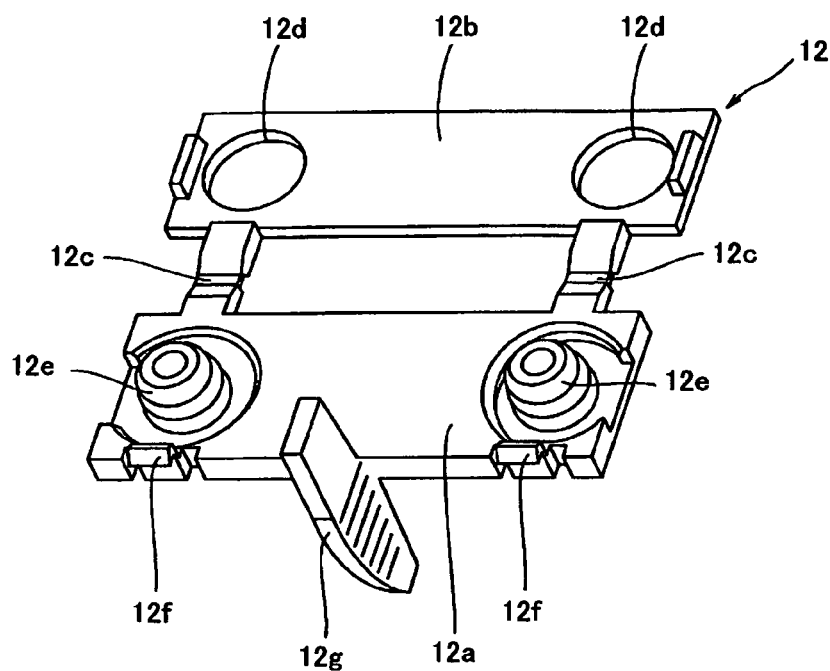
[Fig. 5]
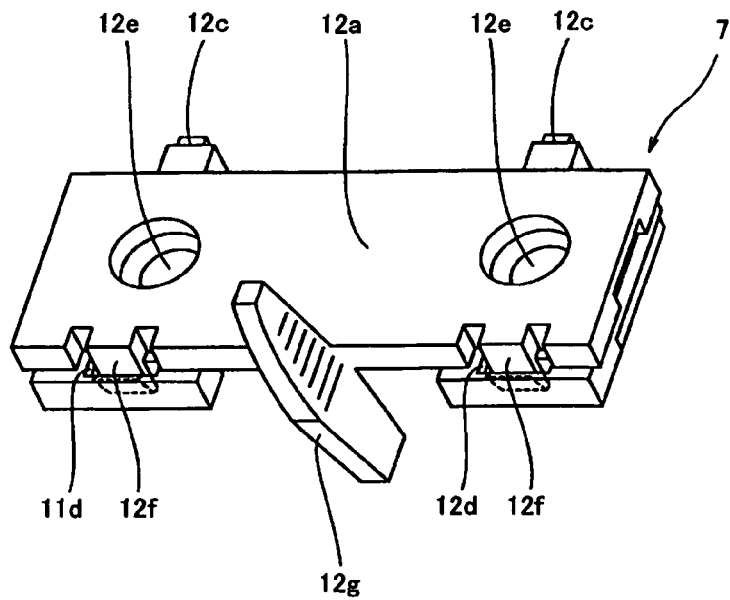

[Fig. 6]
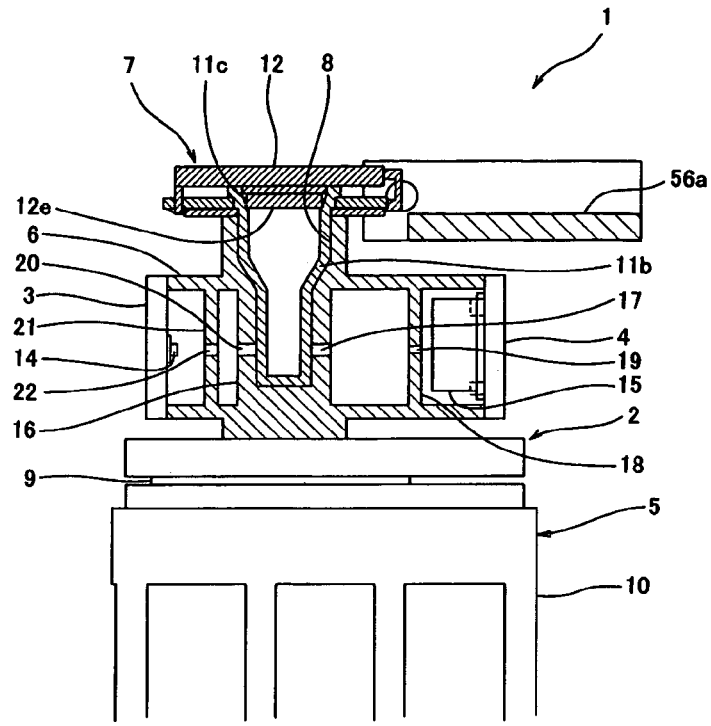
[Fig. 7]
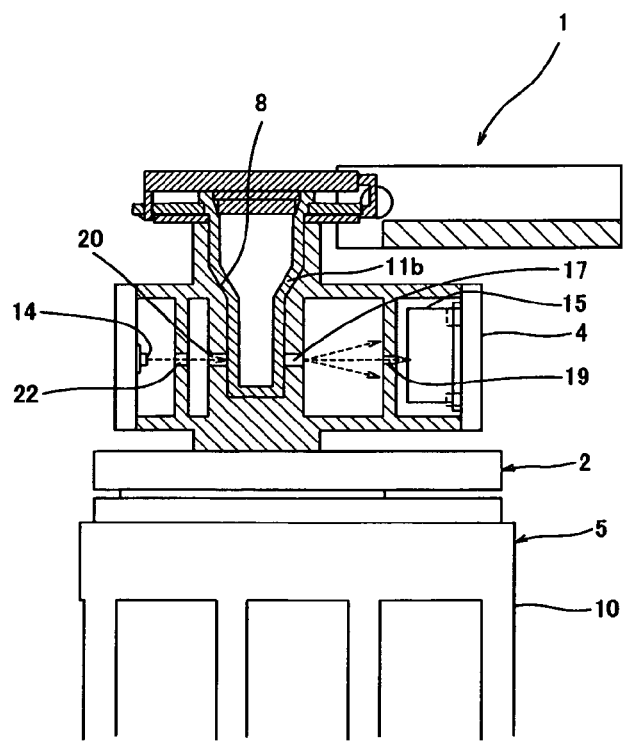

[Fig. 8]
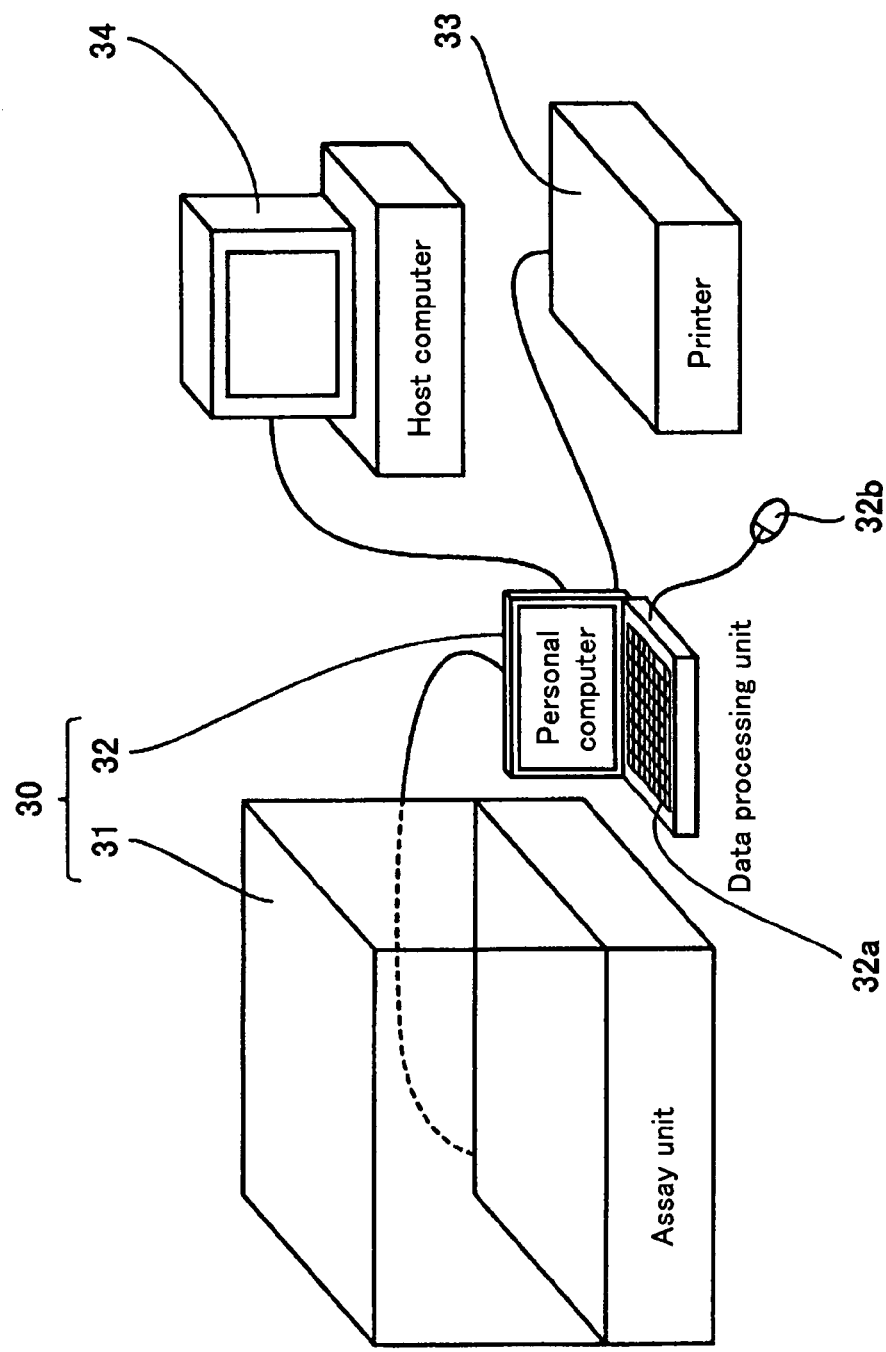

[Fig. 9]
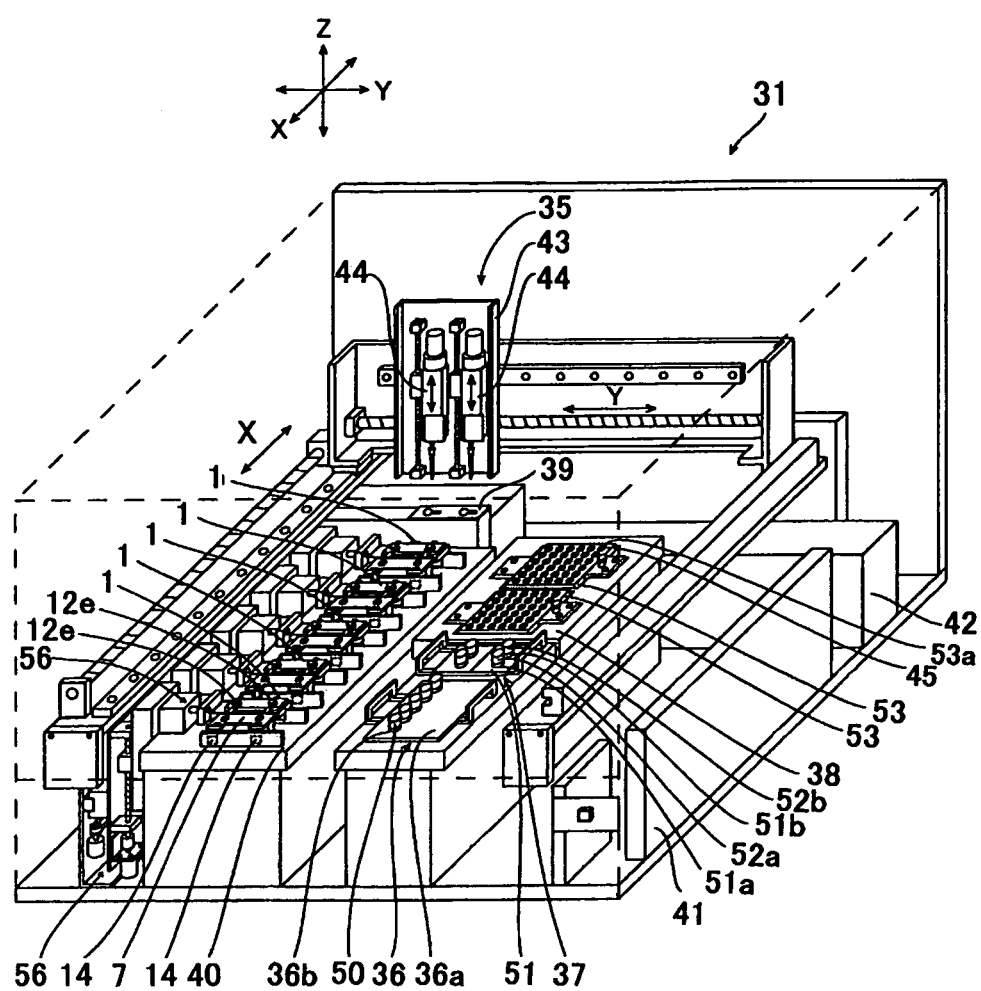

[Fig. 10]
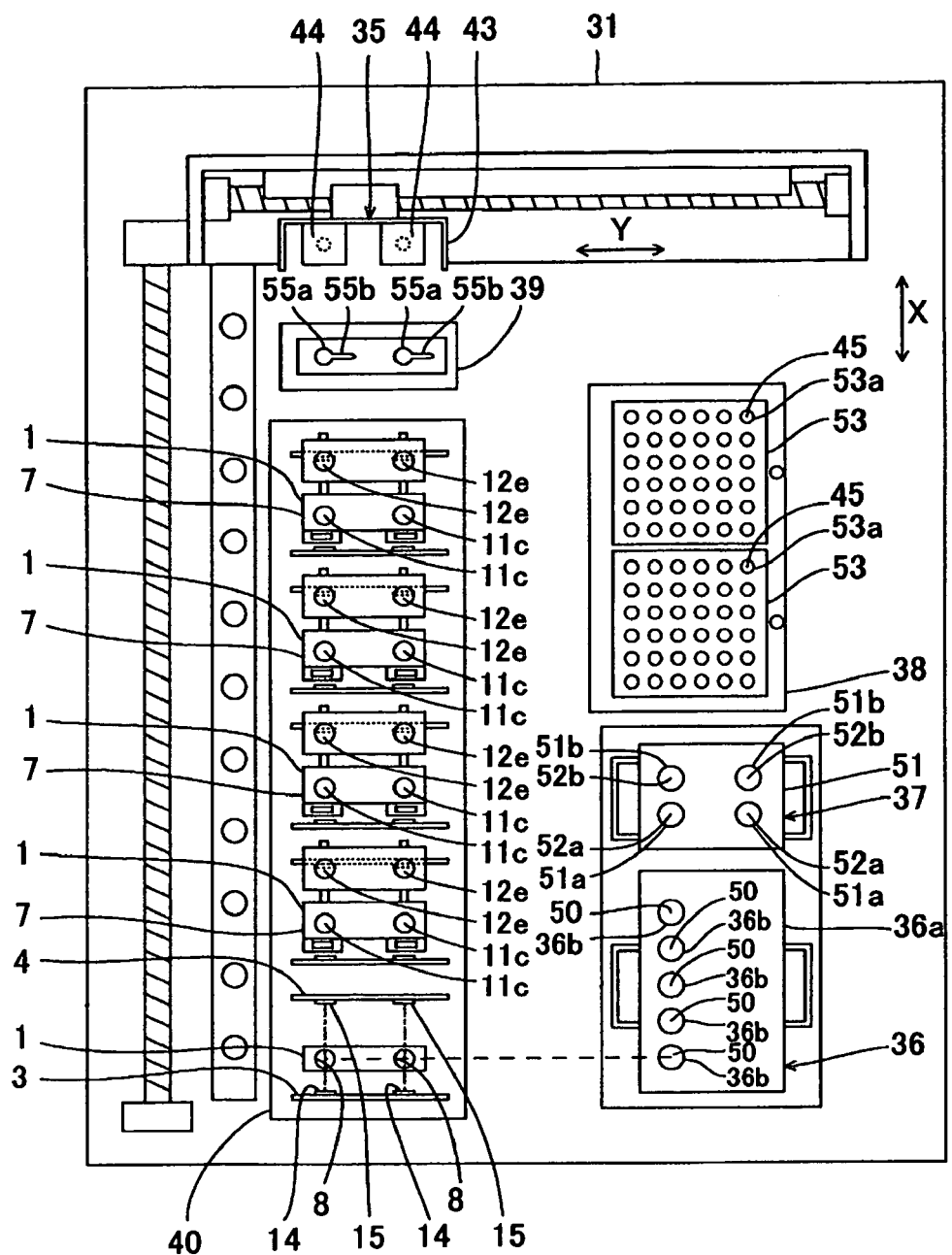

[Fig. 11]
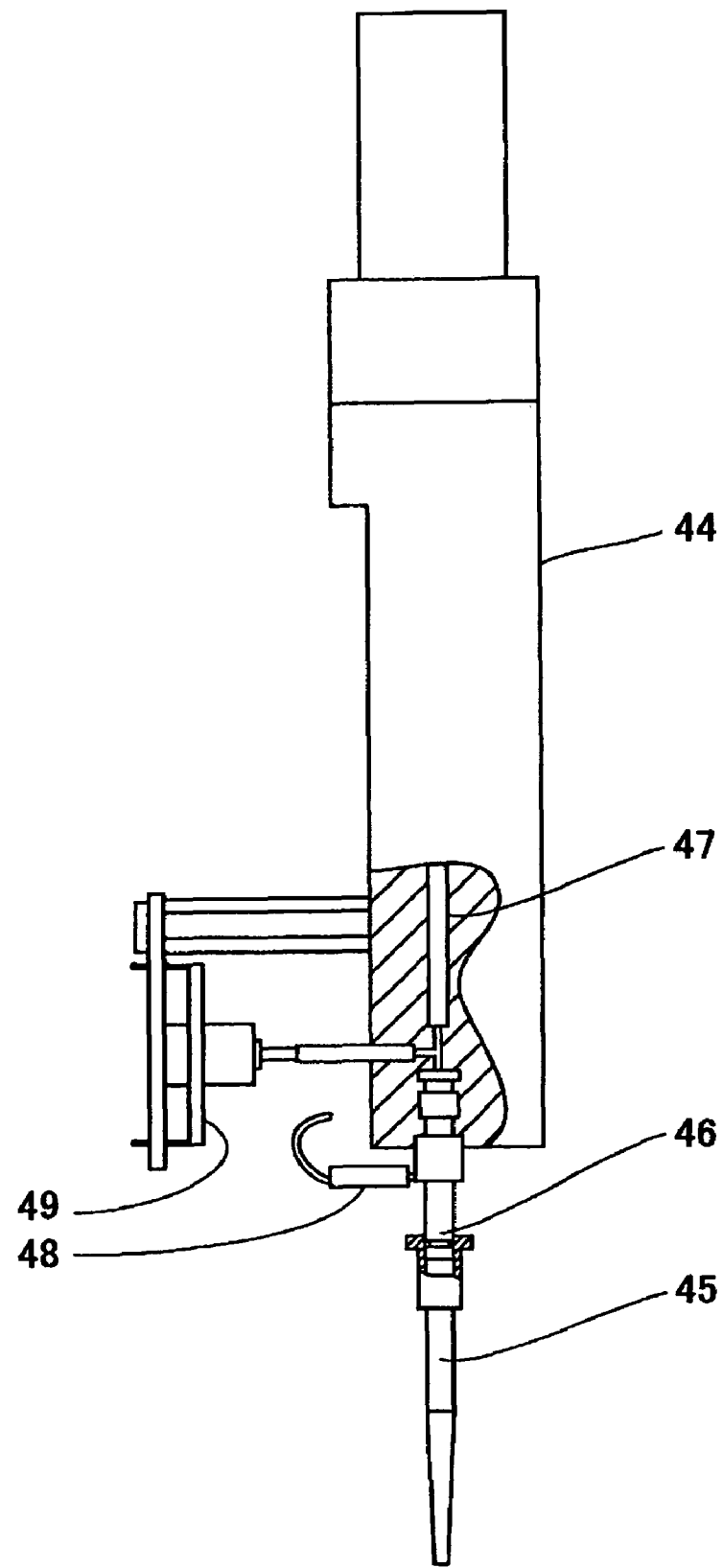

[Fig. 12]
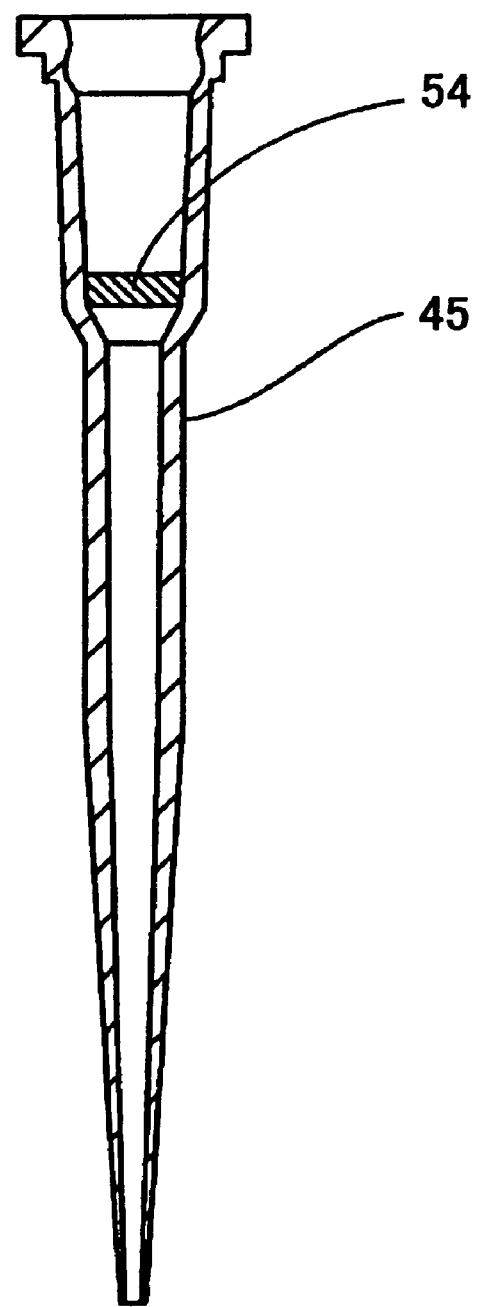

[Fig. 13]
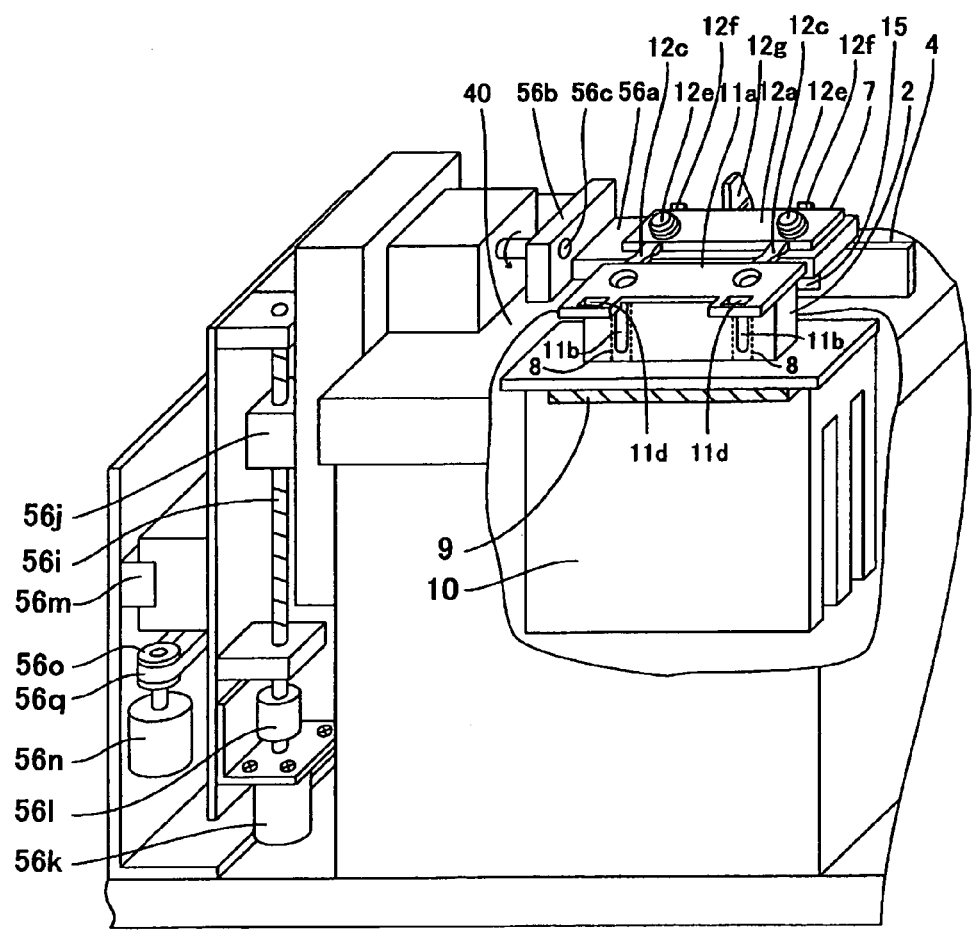

[Fig. 14]
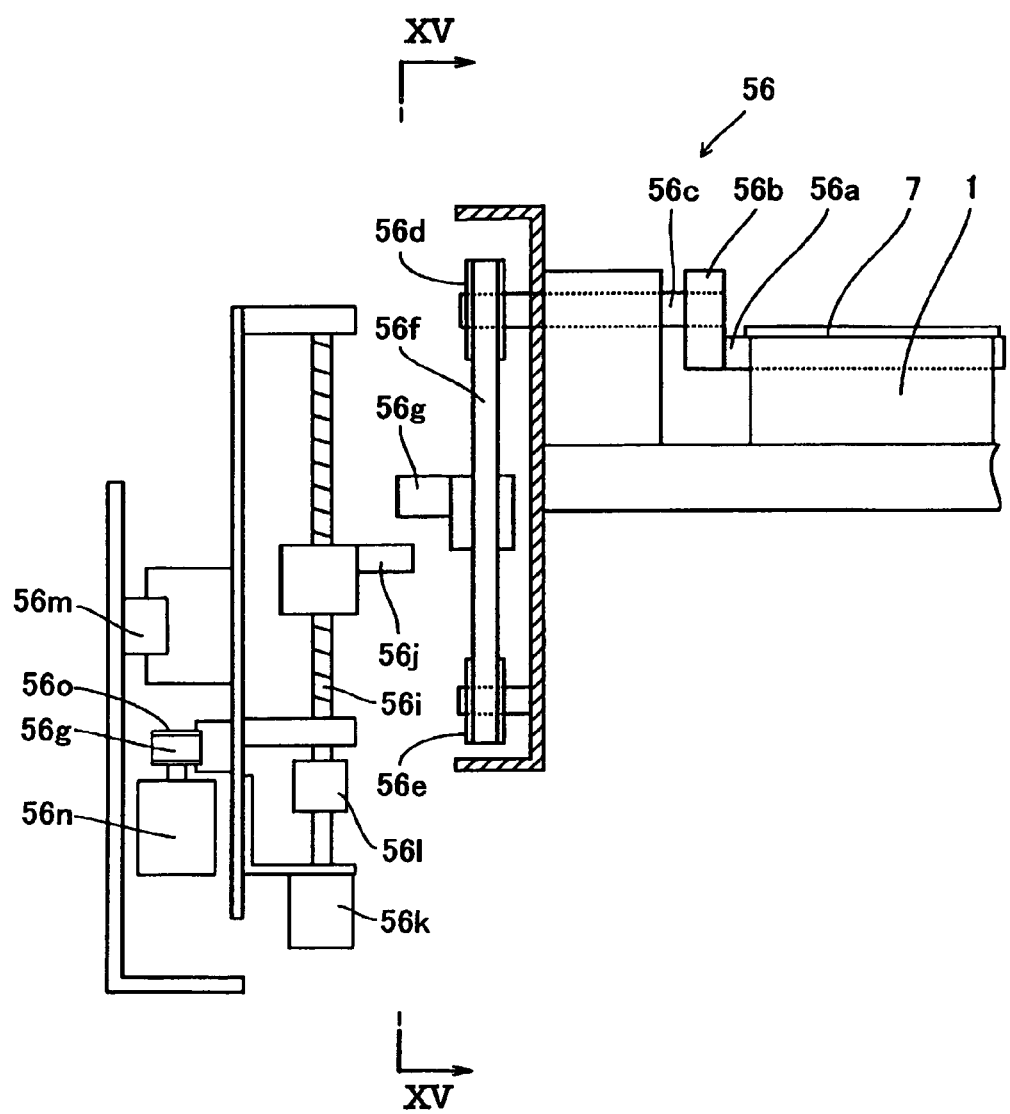

[Fig. 15]
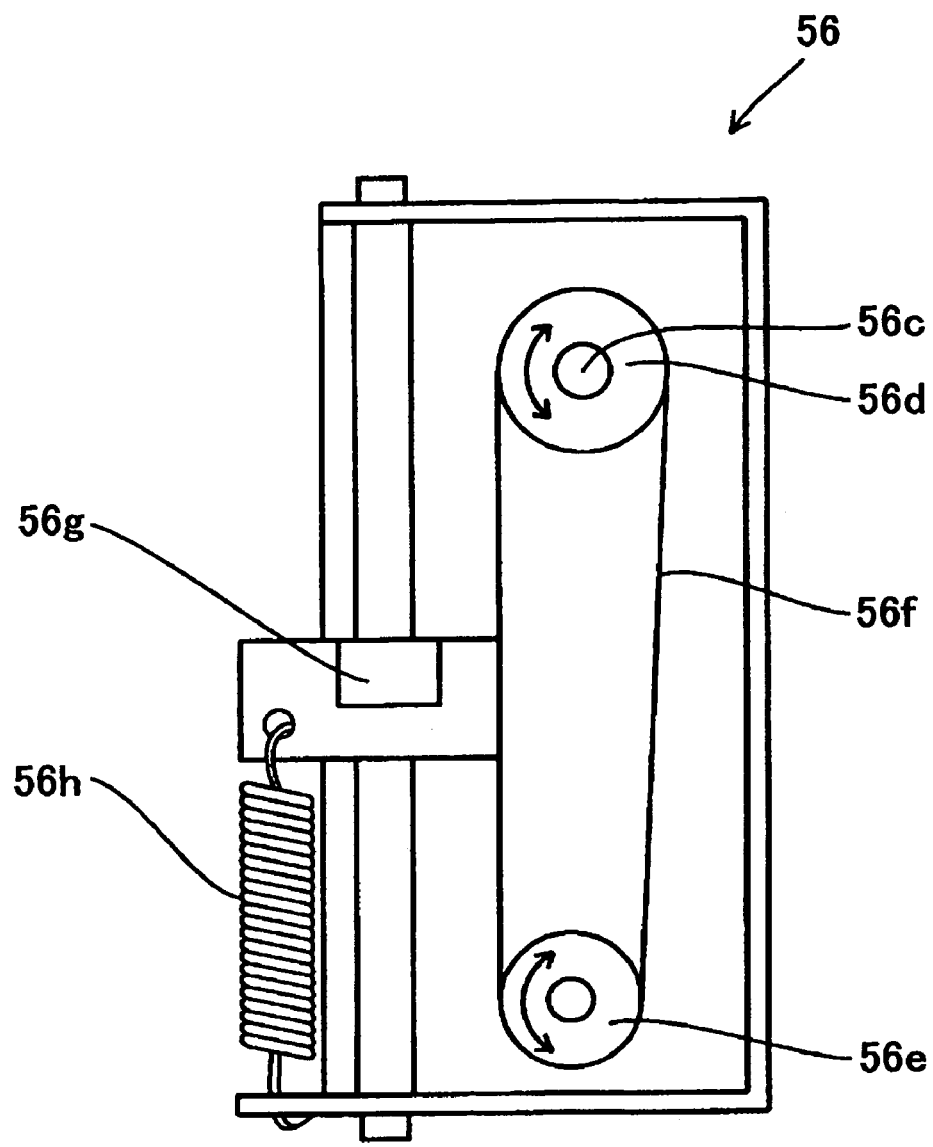

[Fig. 16]
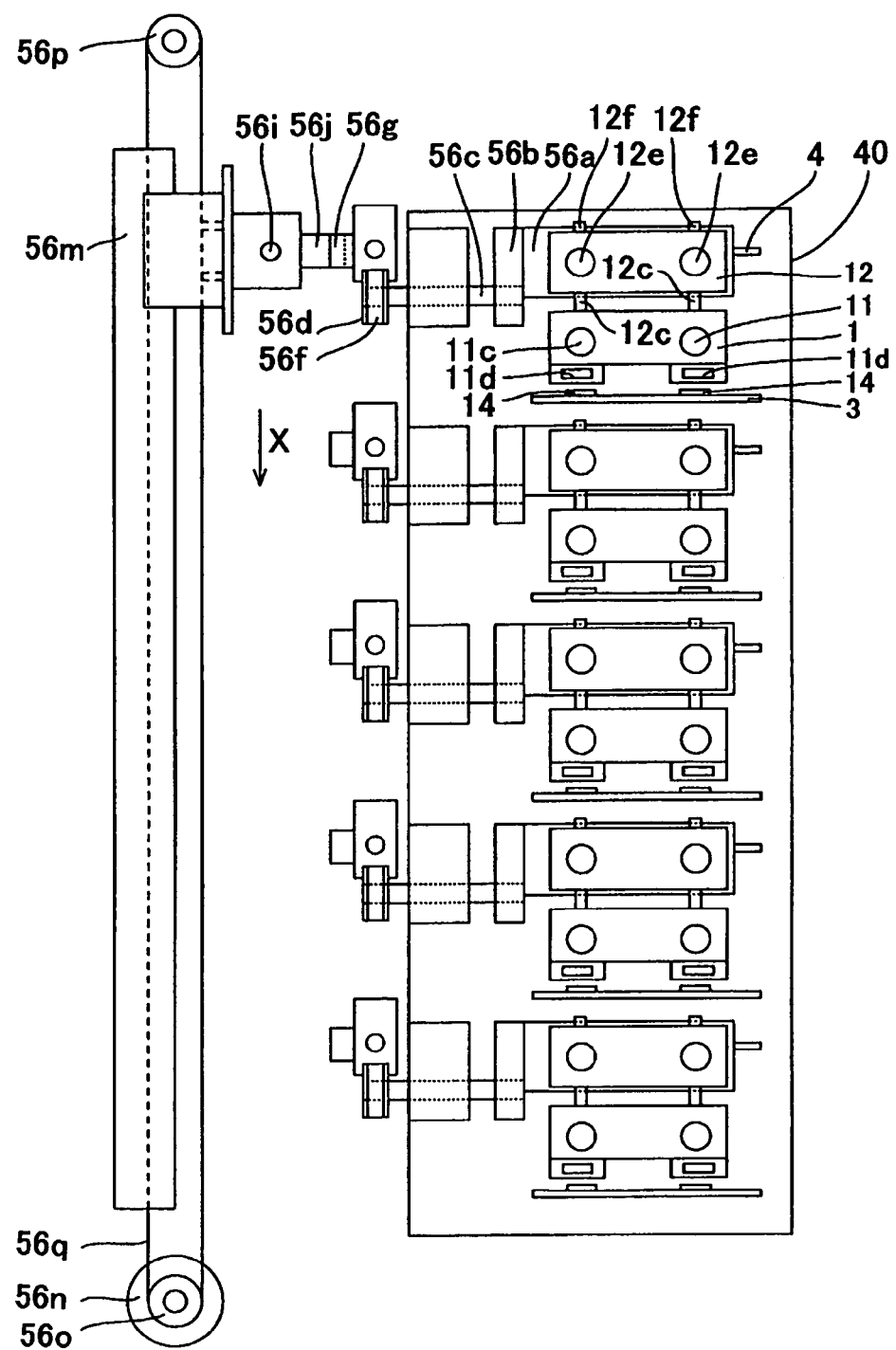

[Fig. 17]
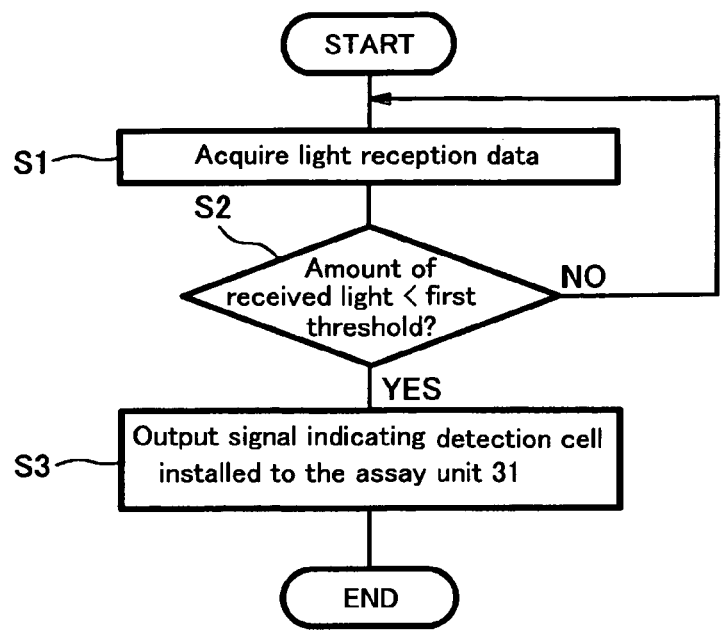
[Fig. 18]
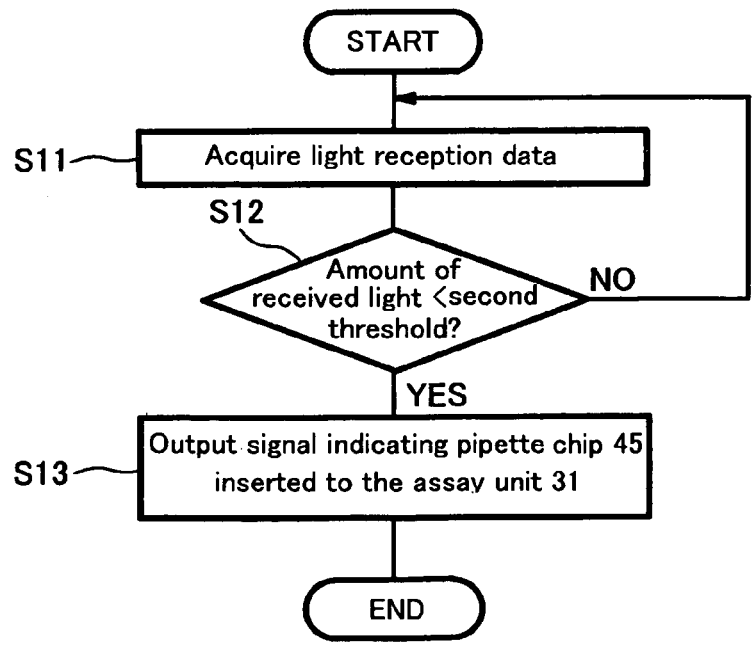

[Fig. 19]
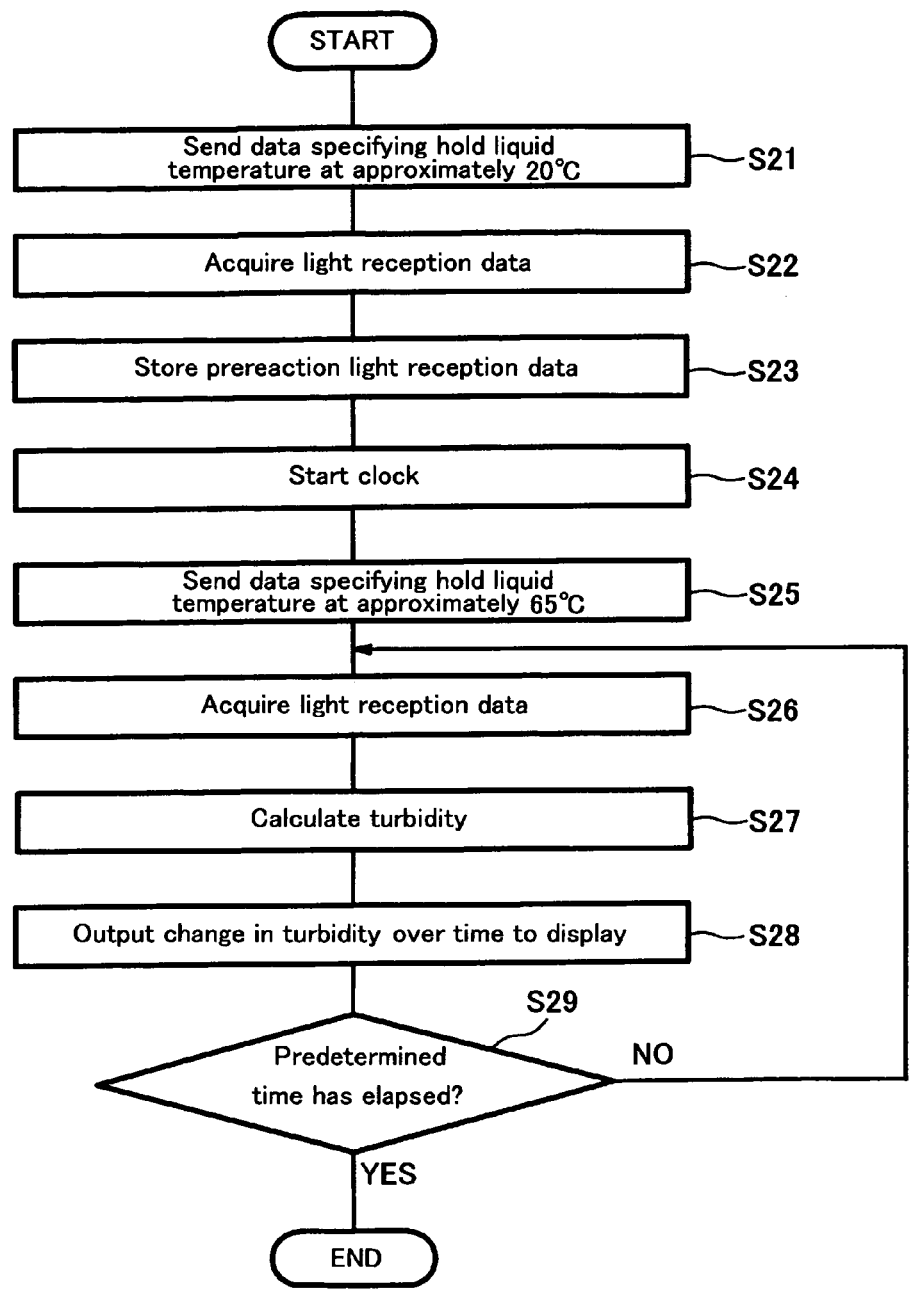

[Fig. 20]
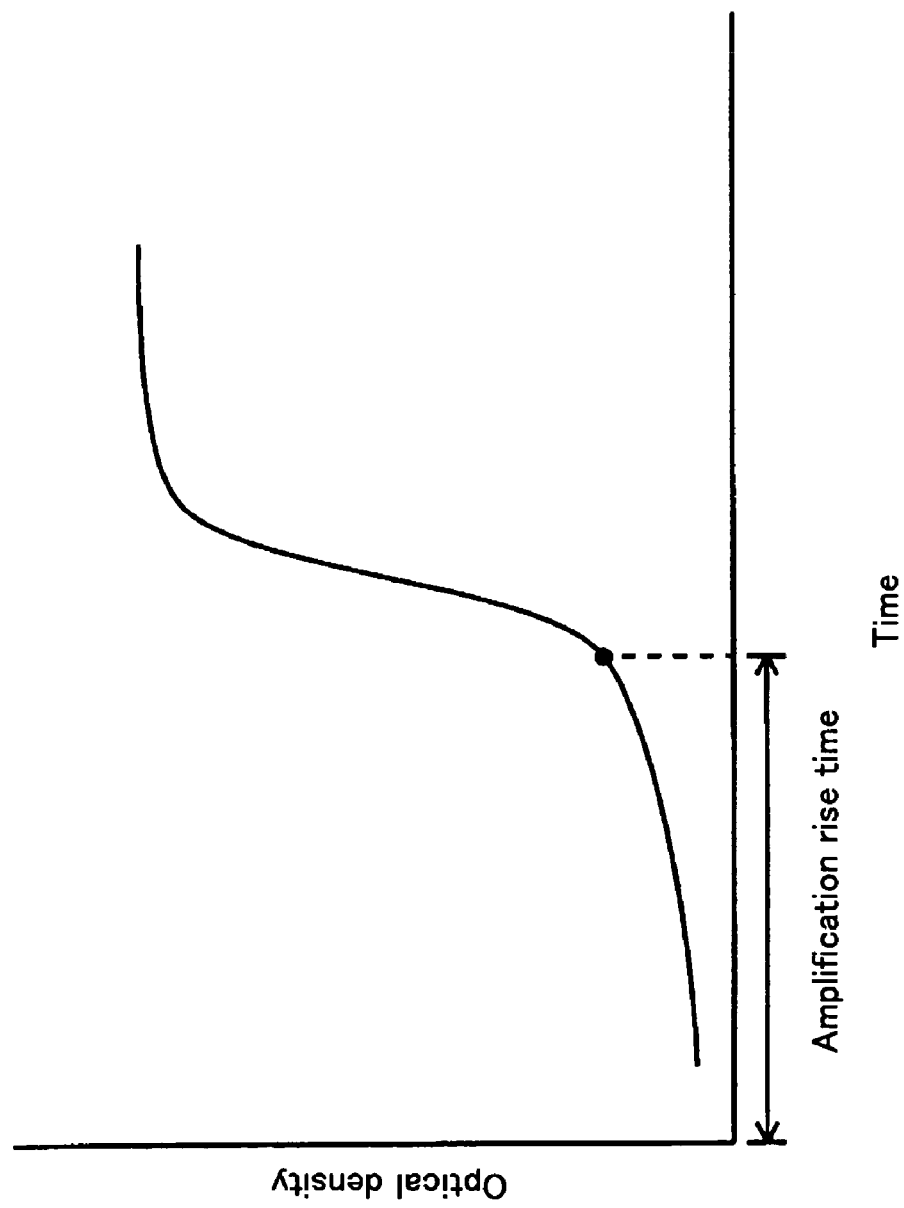

[Fig. 21]
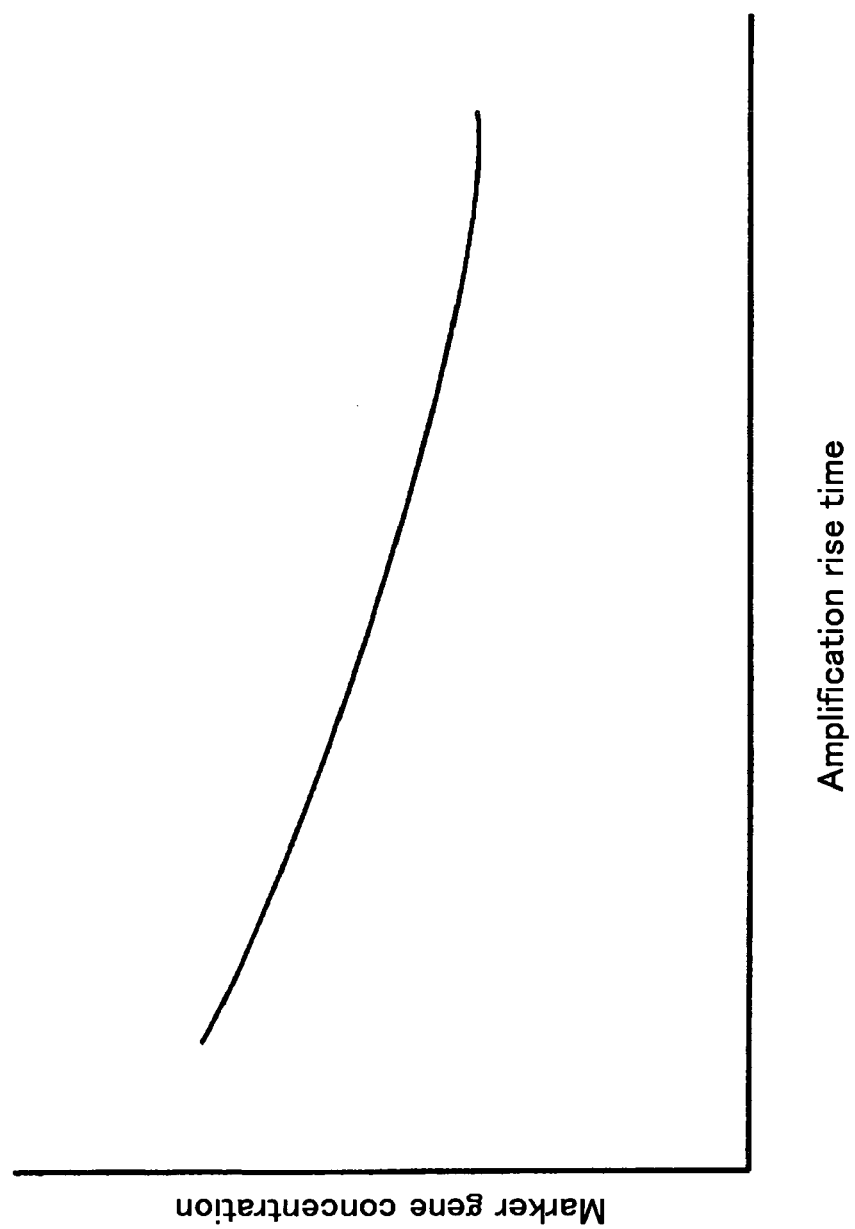

OPTICAL DEVICE AND TURBIDITY DETECTION APPARATUS USING SAME

This application claims priority under 35 U.S.C. §119 to Japanese Patent Application No. 2004-013519 filed Jan. 21, 2004, the entire content of which is hereby incorporated by reference.

FIELD OF THE INVENTION

The present invention relates to an optical device used for detecting a material accommodated in a transparent container, and a turbidity detection apparatus provided with the optical device.

BACKGROUND

Turbidity detection devices for detecting the turbidity of a liquid accommodated in a transparent container, which is the object of turbidity detection, are widely known (for example, refer to Japanese Laid-Open Patent Publication No. 5-133893). The turbidity detection device disclosed in Japanese Laid-Open Patent Publication No. 5-133893 transmits light from a light source through a transparent container and a photoreceptor receives the transmitted light, and the turbidity value of the material subjected to turbidity detection is obtained from the amount of received light. Since the amount of transmitted light passing through the transparent container decreases as the turbidity of the material subjected to turbidity detection increases, it is possible to obtain a turbidity value based on the amount of transmitted light.

In the conventional turbidity detection device mentioned above, however, the amount of light transmitted through the transparent container decreases in conjunction with the turbidity of the material subjected to turbidity detection and the scattered light increases therewith, and since some of the scattered light enters the light-receiving surface of the photoreceptor, the amount of received scattered light increases in conjunction with the increase in turbidity, and this increase generates errors in turbidity detection.

Furthermore, a lens is provided between the transparent container and the photoreceptor to prevent the generation of error, and although it is possible that this lens will prevent the scattered light from entering the photoreceptor, a problem of error generation arises due to the thermal deformation of the lens caused due to temperature when, for example, the turbidity detection device requires temperature management as in the case of nucleic acid detection devices.

SUMMARY

In view of the aforesaid information, an object of the present invention is to provide an optical device which suppresses the generation of detection errors, and a turbidity detection apparatus provided with this optical device.

A first aspect of the present invention is an optical device including a photoemitter for emitting light, a mounting unit for installing a transparent container accommodating a sample to be subjected to detection, a photoreceptor for receiving the light emitted by a photoemitter and transmitted through the transparent container installed in the mounting unit, a first member disposed between the transparent container and the photoreceptor and having a first pinhole through which passes the light transmitted through the transparent container, and a second member disposed between the first member and the photoreceptor and having a second pinhole through which passes the transmitted light that has passed through the first pinhole.

A second aspect of the present invention is an optical device including a photoemitter for emitting light, a mounting unit for installing a transparent container accommodating a sample to be subjected to detection, a photoreceptor for receiving the light emitted by a photoemitter and transmitted through the transparent container installed in the mounting unit, a first member disposed between the photoemitter and the transparent container and having a first pinhole, and a second member disposed between the transparent container and the photoreceptor and having a second pinhole through which passes the light transmitted through the transparent container.

A third aspect of the present invention is a turbidity detection apparatus including a photoemitter for emitting light, a mounting unit for installing a transparent container accommodating a sample to be subjected to turbidity detection, a photoreceptor for receiving the light emitted by a photoemitter and transmitted through the transparent container installed in the mounting unit, a first member disposed between the transparent container and the photoreceptor and having a first pinhole through which passes the light transmitted through the transparent container, a second member disposed between the first member and the photoreceptor and having a second pinhole through which passes the transmitted light that has passed through the first pinhole, and a turbidity detection unit for detecting the turbidity of a sample subjected to turbidity detection and accommodated in the transparent container based on the amount of light received by the photoreceptor.

BRIEF DESCRIPTION OF THE DRAWINGS

FIG. 1 is a perspective view of the general structure of an embodiment of the turbidity detection optical device;

FIG. 2 is a perspective view showing the structure of detection cell of the embodiment;

FIG. 3 is a front cross section view showing the structure of the cell member of the embodiment;

FIG. 4 is a perspective view showing the structure of the cover of the embodiment;

FIG. 5 is a perspective view of the detection cell in the closed cover state;

FIG. 6 is a side section view showing the essential structure of the turbidity detection optical device of the embodiment;

FIG. 7 is a side section view illustrating the operation of the turbidity detection optical device of the embodiment;

FIG. 8 is a schematic perspective view showing the general structure of a nucleic acid detection device of the embodiment;

FIG. 9 is a perspective view showing the structure of the assay unit of the embodiment;

FIG. 10 is a top view showing the structure of the assay unit of the embodiment;

FIG. 11 is a side partial section view of the structure of the syringe unit of the embodiment;

FIG. 12 is a side section view showing the structure of the pipette chip of the embodiment;

FIG. 13 is a perspective view showing the structure of one set of a turbidity detection optical device and cover closing mechanism;

FIG. 14 is a front section view showing the structure of one set of a turbidity detection optical device and cover closing mechanism;

FIG. 15 is a view on the XV-XV line of FIG. 14;

FIG. 16 is a top view showing the structure of the optical detection unit of the embodiment;

FIG. 17 is a flow chart showing the processing sequence of the detection cell installation detection process in the data processing unit of the embodiment;

FIG. 18 is a flow chart showing the processing sequence of the pipette chip insertion detection process in the data processing unit of the embodiment;

FIG. 19 is a flow chart showing the processing sequence of the turbidity detection process in the data processing unit of the embodiment;

FIG. 20 is a graph showing the change in turbidity over time in the amplification reaction by the LAMP method; and FIG. 21 is a graph of the calibration curve showing the relationship between the marker gene density and amplification elevation time in the amplification reaction by the LAMP method.

DETAILED DESCRIPTION OF THE DRAWINGS AND THE PRESENTLY PREFERRED EMBODIMENTS

The optical device and turbidity detection apparatus of an embodiment of the present invention are described hereinafter by way of example referring to the drawings.

In the present embodiment, a nucleic acid detection device (gene amplification detection device) is described as an example of the turbidity detection device. The nucleic acid detection device is an analyzer aiding the diagnosis of cancer metastasis in surgically excised tissue; genes (mRNA) of cancerous origin present in the excised tissue are amplified using the LAMP (loop-mediated isothermal amplification) method, and detected by measuring the turbidity of the liquid generated in conjunction with the amplification. Details of the LAMP method are disclosed in U.S. Pat. No. 6,410,278.

FIG. 1 is a perspective view showing the general structure of the turbidity detection optical device. As shown in FIG. 1, a turbidity detection optical device 1 mainly includes a mounting block 2, light-emitting circuit board 3, light-receiving circuit board 4, and a temperature regulator 5. The mounting block 2 is formed of a metal block, such as aluminum or the like, and on the mounting block 2 are arranged (hereinafter the arrangement direction is referred to as lateral direction) two channels 6 usable for various separate turbidity detection tests. Insertion holes 8 usable for inserting cells 11b of the detection cell 7, which accommodate the material to be subjected to turbidity detection described later, are open on the top of the channels 6.

Before and behind the mounting block 2 are mounted the light-emitting circuit board 3 and light-receiving circuit board 4. In the following description, the direction viewed from the mounting block 2 toward the light-emitting circuit board 3 is designated the front direction, and the direction toward the light-receiving circuit board 4 is designated the back direction. The previously mentioned two channels 6 are each cylindrical in shape and extend in the front-to-back direction; the light-emitting circuit board 3 is mounted at the front end of each channel 6, and the light-receiving circuit board 4 is mounted at the back end of each channel 6.

The temperature regulator 5 is provided below the mounting block 2. The temperature regulator 5 is mainly formed by a square plate-shaped Peltier module 9, and a heat sink 10 formed of a plurality of cooling fins. The top endface of the Peltier module 9 is adhered to the mounting block 2, and the bottom endface of the Peltier module 9 is adhered to the top endface of the heat sink 10. The heat sink 10 is formed of aluminum alloy with excellent cooling characteristics, and the heat sink 10 radiates conducted heat from the Peltier module 9 to outside the device.

FIG. 2 is a perspective view showing the structure of the detection cell 7. As shown in FIG. 2, the detection cell 7 includes two integratedly combined members of a cell member 11 formed of transparent resin (for example, a crystalline olefin thermoplastic resin such as polymethylpentene (TPX)) which has light transmitting characteristics and heat-resistance, and a cover 12 formed of a heat-resistance synthetic resin (for example, high-density polyethylene). The cell member 11 includes integratedly formed connecting plate 11a having an approximate sheet-like shape, and two cells 11b which respectively project from the bottom surface of the connecting plate 11a. The connecting plate 11a is provided with a circular opening 11c at two locations, and the respective cell 11b is connected to the opening 11c. The cell 11b has a cylindrical shape with a hollow interior so as to be capable of holding a liquid, and the external dimensions are slightly smaller than the dimensions of the previously mentioned insertion hole 8. FIG. 3 is a front cross section view showing the structure of the cell member 11. As shown in FIG. 3, an interior wall floor 11e of the cell 11b of the cell member 11 is formed in an approximate U-shape when viewed from the front so as to ensure an adequate height of the liquid surface to be subjected to turbidity detection using the turbidity detection optical device 1 even when a small amount of liquid is used. As shown in FIG. 2, two hook connector holes 11d are provided on the edge of the connecting plate 11a so as to be mutually isolated in a horizontal direction.

FIG. 4 is a perspective view showing the structure of the cover 12. As shown in FIG. 4, the cover 12 mainly includes a rectangular main plate 12a and a rectangular fixed plate 12b which is slightly smaller than the main plate 12a. The main plate 12a is approximately the same size as the previously mentioned connecting plate 11a, and the main plate 12a and fixed plate 12b are linked by two connectors 12c; the connectors 12c are formed with a thin middle section so as to be bendable at the center section. Furthermore, two round holes 12d are provided in the fixed plate 12b. As shown in FIG. 2, a thin and approximately rectangular concavity 11f is formed on the bottom surface of the connecting plate 11a, and the fixed plate 12b is inserted into the concavity 11f and the cell 11b passes through the round hole 12d. The cell 11 and cover 12 are assembled in this way.

As shown in FIG. 4, two covers 12e are provided on the main plate 12a. The covers 12e protrude from the main plate 12a in an approximately disk-like shape on one surface of the main plate 12a, and the disk-like shape is slightly smaller than the opening 11c so as to be capable of engaging the opening 11c. Two hooks 12f are provided so as to be mutually isolated on the edge of the main plate 12a on the side opposite the connectors 12c, and a handle 12g is provided at an intermediate position between the hooks 12f for the user to hold. When the cover 12 is folded by bending at the connectors 12c, the hooks 12f are disposed at positions engaging the respective hook connector holes 11d, and the covers 12e are disposed at positions engaging the respective openings 11c when the cover 12 is folded. FIGS. 2 through 4 used in the above description show the cover 12e of the detection cell 7 removed from the opening 11c below, this state is referred to as the open cover state.

FIG. 5 is a perspective view showing the detection cell 7 when the opening 11c is closed by the cover 12e. When, from the open cover state, the cover 12 is folded so as to bend the connectors 12c, the hooks 12f engage the hook connector holes 11d, and the respective covers 12e are inserted to the opening 11c. In this way the openings 11c of the detection cell 7 are closed by the covers 12e (below, referred to as the closed cover state), such that the openings 11c are sealed by the covers 12e and liquid accommodated in the cell 11b is prevented from leaking to the outside.

The detection cell 7 is then irradiated by an electron beam when packed before shipment so as to avoid having gene amplification adversely affected by resolving enzymes such as human saliva and the like which might possibly have adhered during the manufacturing process of the detection cell 7.

FIG. 6 is a side cross section view showing the essential structure of the turbidity detection optical device. When turbidity detection is executed on an material accommodated in the detection cell 7, the detection cell 7 of the previously described structure is mounted on the turbidity detection optical device 1, as shown in FIG. 6, so that the two cells 11b are respectively inserted in the top insertion holes 8. The insertion holes 8 of the turbidity detection optical device 1 are formed with a size and shape to accommodate the cell 11b without a gap so as to ensure efficient heat conduction between the cell 11b and the mounting block 2. As shown in FIG. 6, a blue color LED 14 is provided at each channel 6 on the light-emitting circuit board 3, and a photodiode photoreceptor 15 is provided at each channel 6 on the light-receiving circuit board 4. A light path for the passage of 465 nm wavelength light emitted from the blue LED 14 is formed between the blue LED 14 and photodiode photoreceptor 15 of each channel 6, and the insertion hole 8 is positioned within this light path. The light path is enclosed by wall surfaces vertically and laterally so as to block exterior light from entering. Furthermore, four pinholes are provided within the light path, such that the light passing through the light path may reach the photodiode photoreceptor 15.

The pinhole installation positions are described below. A first pinhole 17 is provided toward the back from the insertion hole 8 in the wall 16 in which is formed the insertion hole 8 of the mounting block 2. An empty space forming part of the light path is provided toward the back from the first pinhole 17, and a wall 18 is disposed at a position a specific distance behind the first pinhole 17 so as to provide a space therebetween. A second pinhole 19 is provided at the approximate center of the wall 18. The photodiode photoreceptor 15 is arranged a specific distance behind the wall 18 so as to provide an empty space therebetween.

A third pinhole 20 is provided in the wall 16 forward from the insertion hole 8. An empty space forming part of the light path is provided toward the front from the third pinhole 20, and a wall 21 is disposed at a position a specific distance foreword from the third pinhole 20 so as to provide a space therebetween. A fourth pinhole 22 is provided at the approximate center of the wall 21. The blue LED 14 is arranged a specific distance foreword from the wall 21 so as to provide an empty space therebetween.

The blue LED 14, fourth pinhole 22, third pinhole 20, first pinhole 17, second pinhole 19, and photodiode photoreceptor 15 are arranged sequentially front-to-back in a straight line. In the present embodiment, the diameters of the fourth pinhole 22, third pinhole 20, and first pinhole 17 are respectively 1 mm, and the diameter of the second pinhole 19 is 0.5 mm; the shapes of the first pinhole 17 and second pinhole 19 are respectively circular.

FIG. 7 is a side cross section view illustrating the operation of the turbidity detection optical device. The light emitted from the blue LED 14 toward the photodiode photoreceptor 15 passes through the fourth pinhole 22 and third pinhole 20. Since other parts of the light emitted from the blue LED 14 are blocked by the walls 21 and 16, only the light passing through the fourth pinhole 22 and third pinhole 20 reaches the cell 11b inserted in the insertion hole 8. Part of this light is transmitted through the material of turbidity detection accommodated in the cell 11b and advances on the optical axis from the cell 11b toward the back (that is, the straight line through the fourth pinhole 22, third pinhole 20, first pinhole 17, and second pinhole 19), whereas the other part of the light is reflected as scattered light by the components contained in the material subjected to turbidity detection. The transmitted light passes through the first pinhole 17 and second pinhole 19 and reaches the photodiode photoreceptor 15, and the scattered light does not reach the light-receiving surface because the scattered light is blocked by the walls 16 and 18.

Preventing the scattered light from reaching the light-receiving surface can also be considered by arranging one pinhole in front of the photoreceptor element. However, when only one pinhole is provided between the cell 11b and the photodiode photoreceptor 15 and there is a short distance separating the pinhole and the photodiode photoreceptor 15 and the photodiode photoreceptor 15 has a large light-receiving surface, part of the scattered light proceeding in an inclined direction relative to the front-to-back direction may pass through the pinhole and reach the light-receiving surface. Therefore, when only one pinhole is provided between the cell 11b and the photodiode photoreceptor 15, it is necessary to ensure a sufficient distance of separation between the pinhole and the light-receiving surface of the photodiode photoreceptor 15, thus increasing the size of the device.

If a plurality of pinholes are disposed between the cell 11b and the photodiode photoreceptor 15, as in the present embodiment, then even if part of the light scattered by the cell 11b passes through the first pinhole (pinhole 17), most of the scattered light does not pass the latter stage pinhole (second pinhole 19), such that the scattered light is effectively eliminated, and the distance separating the last stage pinhole (second pinhole 19) and the light-receiving surface of the photodiode photoreceptor 15 can be kept short compared to when only a single pinhole is provided.

Accordingly, in the turbidity detection optical device 1 of the present embodiment, light emitted from the blue LED 14 passes through the fourth pinhole 22 and third pinhole 20, and only the light component corresponding to the turbidity of the material subjected to turbidity detection accommodated in the cell 11b inserted in the insertion hole 8 is transmitted through the cell 11b. Therefore, the amount of transmitted light is reduced compared to the amount of light emitted from the blue LED 14, and an analog electric signal corresponding to the amount of transmitted light is output from the photodiode photoreceptor 15. This output signal is input to an external computer or the like for use in detecting the turbidity of the material being subjected to turbidity detection.

The previously mentioned sizes of the first pinhole 17 and second pinhole 19 are given as an example, and are to be suitably set in consideration of the distance between the first pinhole 17 and the cell 11b, the distance between the first pinhole 17 and second pinhole 19, distance between the second pinhole 19 and the photodiode photoreceptor 15 and the like.

Below is described the structure of the nucleic acid detection device (gene amplification detection device) 30 in the turbidity detection device of an embodiment of the present invention installed in the turbidity detection optical device. FIG. 8 is a schematic perspective view of the general structure of the nucleic acid detection device 30 of the embodiment of the present invention. As shown in FIG. 8, the nucleic acid detection device 30 includes an assay unit 31, and a data processing unit 32 connected to the assay unit 31 through a communication line. The data processing unit 32 is a personal computer provided with a keyboard 32a and a mouse 32b. Peripheral devices connected to the data processing unit 32 through a communication line include a printer 33 and host computer 34. The printer 33 is provided to print out graphic data and text data. The host computer 34 receives the assay data output from the data processing unit 32.

FIG. 9 is a perspective view and FIG. 10 is a top view showing the structure of the assay unit 31. As show in FIGS. 9 and 10, the assay unit 31 mainly includes a dispensing mechanism 35, sample container holder 36, reagent container holder 37, chip holder 38, chip disposal unit 39, and optical detection unit 40 which includes five turbidity detection optical devices 1. The assay unit 31 is provided with a microcomputer, which has a controller 41 for controlling the device and controlling the input and output of external devices, and an internal power source for supplying power to the entire device including the controller 41.

The dispensing mechanism 35 has an arm 43 movable in the X-axis and Y-axis directions (horizontal directions), and two syringe units 44 independently movable relative to the arm 43 in the Z-axis direction (vertical direction). FIG. 11 is a partial side section view showing the structure of the syringe unit 44. As shown in FIG. 11, the syringe unit 44 is provided with a nozzle 46 to the tip of which a pipette chip 45 described later can be detachably installed, pump 47, liquid surface sensor 48, and pressure sensor 49. The pump 47 is constructed so as to be capable of suctioning and discharging a fluid from the nozzle 46. The liquid surface sensor 48 is, for example, an electrostatic capacitance sensor, which detects the contact of the tip of the pipette chip 45 formed of conductive resin with the liquid surface. Furthermore, the pressure sensor 49 detects the pressure during suctioning and discharging by the pump 47. Detecting whether or not suction and discharge are reliably executed can be detected by the liquid surface sensor 48 and pressure sensor 49.

As shown in FIGS. 9 and 10, a concavity not shown in the drawing is formed in the sample container holder 36, and a sample container platform 36a is removably inserted in this concavity. A plurality of sample container holes 36b are formed in the sample container platform 36a, and sample containers 50 containing soluble extract (sample) prepared beforehand by processing (homogenizing, filtering, diluting) excised tissue are placed in the sample container holes 36b. Placed in the sample container holes 36b are containers accommodating calibrator including marker genes of a predetermined concentration to be used as a standard for preparing a calibration curve described later, and containers accommodating negative controls for confirming that the device and reagents are not contaminated and the like.

A concavity not shown in the drawing is formed in the reagent container holder 37, and a reagent container platform 51 is removably inserted in this concavity, the platform 51 including two primer reagent container holes 51a and two enzyme reagent container holes 51b. Two primer reagent containers 52a containing two types of primer reagents, and two enzyme reagent containers 52b containing two types of enzyme reagents corresponding to the primer reagents are placed in the primer reagent container holes 51a and the enzyme reagent container holes 51b of the reagent container holder 51. In the present embodiment, a primer reagent container 52a containing cytokeratin 19 (CK19) and an enzyme reagent container 52b containing an enzyme reagent of CK19 are placed in a set of primer reagent container hole 51a in enzyme reagent container hole 51b. Furthermore, a primer reagent container 52a containing β-actin and an enzyme reagent container 52b containing an enzyme reagent of β-actin are placed in the other set of primer reagent container hole 51a and enzyme reagent container hole 51b.

Two concavities not shown in the drawings are provided in the chip holder 38, and two racks 53, which have holes 53a for accepting a plurality of pipette chips 45, are removably inserted in the concavities. FIG. 12 is a side section view showing the structure of the pipette chip 45. The pipette chip 45 is formed of a conductive resin material containing carbon, and a filter 54 provided with vertical through-holes is loaded mod way therein. The filter 54 functions to prevent an erroneous inflow of liquid to the syringe unit 44. The pipette chip 45 is irradiated by an electron beam when packed before shipment so as to avoid having gene amplification adversely affected by resolving enzymes such as human saliva and the like which might possibly have adhered during the manufacturing process of the pipette chip 45.

As shown in FIG. 10, two chip disposal holes 55a are provided in the chip disposal unit 39 for the disposal of used pipette chips 45. A channel 55b which is narrower than the chip disposal hole 55a is provided so as to connect the chip disposal holes 55a.

As shown in FIGS. 9 and 10, five turbidity detection optical devices 1 are mounted on the optical detection apparatus 40. The operation of the Peltier module 9 of the respective turbidity detection optical devices 1 is controlled by the controller 41 so as to maintain the temperature of the liquid within the detection cell 7 in a range of approximately 20-65° C. The analog signal output by the photodiode photoreceptor 15 is subjected to A/D conversion by the controller 41, and is transmitted to the data processing unit 32 as a digital signal.

Five cover closing mechanisms 56 corresponding to the respective turbidity detection optical devices 1 are provided in the optical detection apparatus 40. FIG. 13 is a perspective view showing the structure of one set of turbidity detection optical device 1 and cover closing mechanism 56, and FIG. 14 is a front cross section view of the same. As shown in FIGS. 13 and 14, the cover closing mechanism 56 is provided with a square plate-like cover-closing arm 56a. Installed on the cover-closing arm 56a is a main plate 12a of the previously described cover 12 which is horizontally oriented when the detection cell 7 is in the closed-cover state. The cover-closing arm 56a is fixedly attached to a plate-like rotating member 56b, and a rotating shaft 56c extends from the rotating member 56b. A pulley 56d is attached to the tip of the rotating shaft 56c, and a pulley 56e, which rotatably pivots about the rotating shaft parallel to the rotating shaft 56c, is provided on the body of the assay unit 31, and a belt 56f is reeved between the pulleys 56d and 56e. A vertical moving member 56g is mounted on part of the belt 56f, and the vertical moving member 56g is raised and lowered in conjunction with the rotation of the pulleys 56d and 56e.

FIG. 15 shows a view on the XV-XV line of FIG. 14. As shown in FIG. 15, the top end of a tension spring 56h extending vertically is attached to the vertical moving member 56g, and the bottom end of the tension spring 56h is attached to the body of the assay unit 31. The vertical moving member 56g is held at the position of at-rest length of the tension spring 56h, such that the cover-closing arm 56a is maintained in a horizontal state (that is, the detection cell 7 is in the open cover state). As shown in FIG. 14, a pressing member 56j is disposed at a position in contact with the vertical moving member 56g when it is raised, and the pressing member 56j is moved in a vertical direction using a stepping motor 56k and slide screw 56i. In this way when the pressing member 56j is raised, the vertical moving member 56g is pushed upward against the force exerted by the tension spring 56h, thereby rotating the cover-closing arm 56a. A torque limiter 56l is provided between the stepping motor 56k and the slide screw 56i so as to idle when the torque exceeds a predetermined torque. In this way when the detection cell 7 is in the closed cover state, unnecessary force is not applied to the cover member 12.

FIG. 16 is a top view showing the structure of the optical detection device 40. The pressing mechanism which includes the pressing member 56j, stepping motor 56k, torque limiter 56l and slide screw 56i is mounted to a direct-movement guide 56m so as to be movable in the X-axis direction, as shown in FIG. 16. The pressing mechanism is moved in the X-axis direction between the five turbidity detection optical devices 1 using the stepping motor 56k, pulleys 56o and 56p, and timing belt 56q.

The operation of the nucleic acid detection device 30 of the embodiment of the present invention is described below. In the nucleic acid detection device 30 of the embodiment, gene detection is accomplished, as described previously, by amplifying the genes (mRNA) of cancer origin surgically excised from tissue using the LAMP method, and measuring the turbidity of the liquid generated in conjunction with the amplification.

As shown in FIGS. 9 and 10, a sample container 50, which contains a soluble extract liquid (sample) prepared beforehand by processing (homogenizing, filtering, diluting) excised tissue, is placed by the user in the sample container hole 36b of the sample container platform 36a. The user then places the primer reagent container 52 containing CK19 (cytokeratin 19) and the enzyme reagent container 52b containing CK19 and enzyme reagent in the front left side primer reagent container hole 51a and enzyme reagent container hole 51b. The user then places the primer reagent container 52 containing β-actin and the enzyme reagent container 52b containing β-actin and enzyme reagent in the front right side primer reagent container hole 51a and enzyme reagent container hole 51b. The user then inserts two racks 53 respectively holding 36 disposable pipette chips 45 in the concavities of the chip holder 38. In this case, since the initial position of the arm 43 of the dispensing mechanism 35 is a distance above the chip holder 38, as shown in FIGS. 9 and 10, the two racks 53 can easily be placed in the concavities of the chip holder 38. The user places the two cells 11b of the detection cell 7 in the two insertion holes 8 of each turbidity detection optical device 1.

The user starts the assay unit 31 using the keyboard 32a or mouse 32b after recording the assay criteria and samples using the keyboard 32a or mouse 32b of the data processing unit 32 shown in FIG. 8.

When the operation of the assay unit 31 starts, first, the installation of the detection cell 7 in the turbidity detection optical device 1 is detected by the data processing unit 32. Specifically, the detection cell 7 installation detection process is executed as described below.

When the assay unit 31 is operating, the blue LED 14 of the turbidity detection optical device 1 normally emits light. The amount of light received by the photodiode photoreceptor 15 changes in front of and behind the installed detection cell 7. That is, when a cell 11b is not inserted in the insertion hole 6, the light emitted from the blue LED 14 is transmitted through the insertion hole 8 without attenuation, and arrives at the photodiode photoreceptor 15. However, when a cell 11b is inserted in the insertion hole 8, although the light emitted from the blue LED 14 is transmitted through the cell 11b, the amount of light is attenuated by passing through the cell 11b, and the amount of light that reaches the photodiode photoreceptor 15 is less than before the cell 11b was inserted. FIG. 17 is a flow chart showing the processing sequence of the detection cell 7 installation detection process in the data processing unit 32. The data representing the amount of light received by the photodiode photoreceptor 15 is sent to the data processing unit 32 at predetermined intervals (step S1), and the data processing unit 32 compares the amount of received light to a predetermined first threshold value based on the received data (step S2). In step S2, when the amount of received light is equal to or more than the first threshold value (NO in step S2 of FIG. 17), it is determined that a cell 11b is not inserted in the insertion hole 8, and the routine returns to step S1. When the amount of received light is less than the first threshold value in step S2 (YES in step S2 of FIG. 17), the data processing unit 32 determines that a cell 11b is inserted in the insertion hole B, that is, that a detection cell 7 is installed in the turbidity detection optical device 1, and a signal indicating normal installation of the detection cell 7 is sent to the assay unit 31 (step S3), and the process ends. Installation of the detection cell 7 is detected in this way.

After the signal output from the data processing unit 32 in step S3 is received by the controller 41 of the assay unit 31, the assay unit 31 operates as described below. The arm 43 of the dispensing mechanism 35 is moved from the initial position to the chip holder 38, and thereafter the two syringe units 44 of the dispensing mechanism 35 are lowered to the chip holder 38. As shown in FIG. 11, the tips of the nozzles 46 of the two syringe units 44 are pressed into the top opening of the two pipette chips 45, so as to automatically install a pipette chip 45 on the tip of the nozzle 46 of the two syringe units 44. After the two syringe units 44 are lifted, the arm 43 of the dispensing mechanism 35 is moved in the X-axis direction above the two primer reagent containers 52c containing CK19 and β-actin primer reagent placed on the reagent container platform 51. The tips of the two pipette chips 45 installed in the nozzles 46 of the two syringe units 44 are inserted to the liquid surface of the primer reagents CK19 and β-actin contained in the two primer reagent containers 52a by lowering the two syringe units 44. Then, the primer reagents CK19 and β-actin contained in the two reagent containers 52a are suctioned by the pump 47 of the syringe unit 44. When suctioning the primer reagent, the contact of the tip of the pipette chip 45 formed of conductive resin with the liquid surface is detected by the liquid surface sensor 48 (refer to FIG. 11), and the pressure during suctioning by the pump is detected by the pressure sensor 49 (refer to FIG. 11). Whether or not the suction is reliably accomplished is detected by the liquid surface sensor 48 and the pressure sensor 49.

After suctioning the primer reagent, and lifting the two syringe units 44, the arm 43 of the dispensing mechanism 35 is raised above the turbidity detection optical device 1 positions at the innermost side (front inner side device). This time, the arm 43 of the dispensing mechanism 35 is moved so as to not pass above the other second through fifth turbidity detection optical devices 1. In the innermost turbidity detection optical device 1, two pipette chips 45 loaded in the nozzles 46 of the two syringe units 44 are inserted into the two cells 11b of each detection cell 7 by lifting the two syringe units 44. This time, specifically, the pipette chip 45 insertion detection process is performed as described below.

The amount of light received by the photodiode photoreceptor 15 changes in front of and behind the pipette chip 45. That is, when a pipette chip 45 is not inserted in the cell 11b, the light emitted from the blue LED 14 is transmitted through the cell 11b without attenuation, and reaches the photodiode photoreceptor 15. However, when a pipette chip 45 is inserted in the cell 11b, part of the light or all of the light emitted from the blue LED 14 is blocked by the pipette chip 45, such that the amount of light received by the photodiode photoreceptor 15 is less than before insertion. FIG. 18 is a flow chart showing the processing sequence of the pipette chip 45 insertion detection process in the data processing unit 32. The data representing the amount of light received by the photodiode photoreceptor 15 is sent to the data processing unit 32 at predetermined intervals (step S11), and the data processing unit 32 compares the amount of received light to a predetermined second threshold value based on the received data (step S12). In step S12, when the amount of received light is equal to or more than the second threshold value (NO in step S12 of FIG. 18), it is determined that a pipette chip 45 is not inserted in the cell 11b, and the routine returns to step S11. When the amount of received light is less than the second threshold value in step S12 (YES in step S12 of FIG. 18), the data processing unit 32 determines that a pipette chip 45 is inserted in the cell 11b, that is, that a detection cell 7 is installed in the turbidity detection optical device 1, and a signal indicating normal insertion of the pipette chip 45 is sent to the assay unit 31 (step S31), and the process ends. Insertion of the pipette chip 45 in the cell 11b is detected in this way.

After the controller 41 of the assay unit 31 receives the signal output from the data processing unit 32 in step S13, the CK19 and β-actin primer reagents are discharged into the two cells 11b using the pumps 47 of the syringe units 44. During discharge, the contact of the tip of the pipette chip 45 formed of conductive resin with the liquid surface is detected by the liquid surface sensor 48, and the pressure during suctioning by the pump is detected by the pressure sensor 49, just as when suctioning. Whether or not the discharge is reliably accomplished is detected by the liquid surface sensor 48 and the pressure sensor 49. Moreover, detection of suction and discharge is similarly accomplished by the liquid surface sensor 48 and pressure sensor 49 for the subsequent suction and discharge of the enzyme reagent and sample.

After discharge of the primer reagent and the lifting of the two syringe units 44, the arm 43 of the dispensing mechanism 35 is moved in the X-axis direction above the chip disposal unit 39. The pipette chip 45 is disposed of in the chip disposal unit 39. Specifically, the pipette chips 45 are inserted into the two chip disposal holes 55a (refer to FIG. 10) of the chip disposal unit 39 by lowering the two syringe units 44. In this state, the pipette chips 45 are moved below the channel 55b by moving the arm 43 of the dispensing mechanism 35 in the Y-axis direction. Then, the flange on the top surface of the pipette chip 45 is forced downward by contact with the bottom surface on the bilateral sides of the channel 55b by lifting the two syringe units 44, and the pipette chips 45 are automatically removed from the nozzles 46 of the two syringe units 44. The pipette chips 45 are disposed of in the disposal unit 39 in this way.

After the arm 43 of the dispensing mechanism 35 is again moved to the chip holder 38, two new pipette chips 45 are automatically installed in the tips of the nozzles 46 of the two syringe units 44 by the previously described operation in the chip holder 38. Then, the arm 43 of the dispensing mechanism 35 is moved in the X-axis direction above the two enzyme reagent containers 52b containing CK19 and β-actin enzyme reagents placed on the reagent container platform 51. Then, after the two enzyme reagents CK19 and β-actin in the two enzyme reagent containers 52b have been suctioned by lowering the two syringe units 44, the two syringe units 44 are raised. After the arm 43 of the dispensing mechanism 35 is lifted above the turbidity detection optical device 1 on the innermost side, the CK19 and β-actin enzyme reagents are discharged into the respective two cells 11b of the detection cell 7. In this case also, the arm 43 of the dispensing mechanism 35 is moved so as to not pass over the other second through fifth turbidity detection optical devices 1 counting from the inner side. After enzyme reagent discharge, the arm 43 of the dispensing mechanism 35 is moved above the chip disposal unit 39, and the pipette chips 45 are subsequently disposed.

After the arm 43 of the dispensing mechanism 35 is again moved to the chip holder 38, two new pipette chips 45 are automatically installed in the tips of the nozzles 46 of the two syringe units 44. Then, the arm 43 of the dispensing mechanism 35 is moved in the X-axis direction above the sample container 50 containing a sample placed on the sample container holder 36a, and the sample in the sample container 50 is suctioned. Specifically, after one syringe unit 44 positioned above one sample container 50 is lowered and the sample suctioned, that syringe unit 44 is raised. Thereafter, the arm 43 of the dispensing mechanism 35 moves in the Y-direction so as to position the other syringe unit 44 above the same sample container 50. After the other syringe unit 44 is lowered and sample suctioned from the same sample container 50, this other syringe unit 44 is raised. Thereafter the arm 43 of the dispensing mechanism 35 is moved above the innermost turbidity detection optical device 1, the two syringe units 44 are lowered, and the identical samples are discharged into two cells 11b of the detection cell 7. This time also, the arm 43 of the dispensing mechanism 35 moves so as to not pass over the other second through fifth turbidity detection optical devices 1 counting from the inner side.

When sample is discharged, the CK19 and β-actin primer reagents and enzyme reagents and samples contained in the two cells 11b are mixed in the two cells 11b of the detection cell 7 by a plurality of repetitions of the suction and discharge operations using the pumps 47 of the two syringe units 44. When dispensing the primer reagent, enzyme reagent, and sample, the temperature of the liquid within the detection cell 7 is maintained at 20° C. using the Peltier module 9 shown in FIG. 13. Thereafter, the arm 43 of the dispensing mechanism 35 moves above the chip disposal unit 39, and disposal of the pipette chips 45 is accomplished.

After the primer reagent, enzyme reagent, and sample have been discharged into the cell 11b, the cover closing operation of the detection cell 7 is performed. In the cover closing operation, the slide screw 56i is rotated by actuating the stepping motor 56k to rotate in a predetermined direction from the open cover state of the detection cell 7. Since the pressing member 56j is raised in this manner, the vertical moving member 56g (refer to FIG. 14) is raised against the force exerted by the tension spring 56h (refer to FIG. 15). The upward movement of the vertical moving member 56g is converted to the rotational movement of the shaft 56c through the belt 56f and pulley 56d. In this way the rotating member 56b mounted on the shaft 56c pivots on the shaft 56c, and the rotation closes the cover, such that cover-closing arm 56a mounted on the rotating shaft 56b also pivots on the shaft 56c in the same direction. Therefore, the main plate 12a of the cover 12 of the detection cell 7 installed on the cover-closing arm 56a is rotated to the cell 11b side of the detection cell 7, and the opening 11c of the cell 11b is sealed by the cover 12e of the main plate 12a. When the opening 11c is closed by the cover 12e, excessive force applied to the cover 12e or cell 11b is suppressed by idling produced by the torque limiter 56l shown in FIG. 14 when more than a fixed force is applied. In this way damage or deformation of the cover 12e or cell 11b can be prevented during the cover closing operation. When the opening 11c is once closed by the cover 12e, reopening of the cover 12e is prevented by maintaining the state wherein the opening 11c is closed by the cover 12e by having the hooks 12f engage the hook holes 11d.

Thereafter, the vertical moving member 56g (refer to FIG. 14) is lowered by the force exerted by the tension spring 56h by moving the pressing member 56j downward by actuating the stepping motor 56k to rotate in a predetermined direction as show n in FIGS. 13 and 14. Since the shaft 56c is rotated in the opposite direction in this way, the rotating member 56b mounted on the shaft 56c pivots on the shaft 56c and rotates in the opposite direction to the direction when closing the cover. Therefore, the rotating member 56b and the cover-closing arm 56a return to the initial position. The cover closing operation is performed in this way. The cover closing operation of the detection cell 7 is performed after the primer reagent, enzyme reagent, and sample have been discharged into the detection cell 7 of the innermost turbidity detection optical device 1, and before the primer reagent, enzyme reagent, and sample have been discharged into the detection cell 7 of the second turbidity detection optical device 1 counting from the inner side.

After the cover closing operation is completed, the marker gene (mRNA) is amplified by the LAMP (gene amplification) reaction by increasing the temperature of the liquid within the detection cell 7 from approximately 20° C. to approximately 65° C. using the Peltier module 9 shown in FIG. 13. Then, turbidity, which is produced by magnesium pyrophosphate amplification product generated in conjunction with amplification, is detected by a nephelometric method. FIG. 19 is a flow chart showing the processing sequence of the turbidity detection process in the data processing unit 32. Specifically, as shown in FIG. 7, light from the blue LED 14 irradiates the cell 11b from behind. Then, the light transmitted through the cell 11b is received by the photodiode photoreceptor 15. As previously mentioned, a signal representing the amount of light received by the photodiode photoreceptor 15 is sent periodically to the data processing unit 32. The data processing unit 32 sends data specifying that the temperature of the liquid within the detection cell 7 should be maintained at approximately 20° C. to the controller 41 of the assay unit 31 (step S21), and the controller 41 which has received the data controls the operation of the Peltier module 9 as to maintain the liquid temperature at approximately 20° C. Then, the data processing unit 32 acquires the light reception data (step S22), and the amount of received light indicated by the initially received data are stored in memory as prereaction amount of received light (step S23).

Next, the data processing unit 32 starts the clock (step S24), sends data specifying that the temperature of the liquid in the detection cell 7 should be maintained at approximately 65° C. to the controller 41 of the assay unit 31 (step S25), and the controller 41 which has received the data controls the operation of the Peltier module 9 to increase the liquid temperature to 65° C., and maintain this temperature. Then, the data processing unit 32 acquires the light reception data (step S26), designates the amount of received light indicated by the acquired light reception data as the post-reaction amount of received light, and calculates the turbidity=−log {(post-reaction amount of light)/(prereaction amount of light)} (step S27). The data processing unit 32 outputs a graph representing the change in turbidity over time to the display (output updated for second and subsequent) (step S28), and determines whether or not the a predetermined time has elapsed since the clock started (for example 15 minutes) (step S29). When it is determined that the predetermined time has not elapsed in step S29 (Step S29: NO in FIG. 19), the data processing unit 32 returns to the process of step S26. When it is determined that the predetermined time has elapsed in step S22 (step S22: YES in FIG. 19), the process ends.

The processing unit 32 detects (monitors) in real time the turbidity of the liquid in the cell 11b of the detection cell 7 during the amplification reaction. FIG. 20 is a graph of a calibration curve showing the relationship between the marker gene concentration and amplification rise time in the amplification reaction. Assay data of the data processing unit 32 from experimental results are shown in FIG. 20 when time is plotted on the horizontal axis and turbidity (optical density, OD) is plotted on the vertical axis. The amplification rise time, that is, the time until a rapid rise in replication of the marker gene (mRNA) in the sample, is detected from the assay data based on the change in turbidity. As shown in FIG. 21, the concentration of the marker gene is calculated from the amplification rise time based on a calibration curve prepared beforehand from calibration assay results. The calibration curve shown in FIG. 21 is a curve plotting the amplification rise time on the horizontal axis, and plotting the marker gene concentration on the vertical axis; in general the marker gene concentration increases as the amplification rise time decreases.

A container containing a calibrator including the marker gene in a predetermined concentration as a standard for preparing the calibration curve, and a container containing a negative control for confirming the normal non-amplification of a gene that should not amplify are placed in the sample container holes 36b of the sample container platform 36a at a predetermined frequency. The calibrator and negative control are subjected to identical sample suction, discharge, and detection operations as described above. The normal non-amplification of the gene that should not amplify can be confirmed by preparing a calibration curve and performing a detection operation on the negative control.

As described above, a marker gene is detected by the turbidity detection optical device 1 positioned on the innermost side. The turbidity detection optical device 1 second from the inner side can perform a primer reagent, enzyme reagent, and sample dispensing operations, cover closing operation, and marker gene detection operation in parallel with the marker gene detection operation following the cover-closing operation of the turbidity detection optical device 1 on the innermost side. The turbidity detection optical device 1 third from the inner side can perform a primer reagent, enzyme reagent, and sample dispensing operations, cover closing operation, and marker gene detection operation in parallel with the marker gene detection operation following the cover-closing operation of the turbidity detection optical device 1 second from the inner side. Thereafter, the turbidity detection optical devices 1 fourth and fifth from the inner side may sequentially perform similar operations. Counting from the inner side, when performing the cover closing operation in the second through fifth turbidity detection optical devices 1, the pressing mechanism may sequentially move from the innermost turbidity detection optical device 1 through the second through fifth turbidity detection optical devices 1 to perform the cover closing operation by actuating the stepping motor 56n shown in FIG. 16. The detection operation ends at the moment the marker gene detection operation ends for the fifth turbidity detection optical device 1. Thereafter, the user grips the handle of the detection cell 7 and disposes of the five detection cells 7.

In the turbidity detection optical device and turbidity detection apparatus of the embodiment of the present invention as described above, the first pinhole 17 and second pinhole 19 eliminate scattered light, and the light transmitted through the cell 11b reaches the photodiode photoreceptor 15, thereby suppressing the generation of errors due to scattered light. Since a lens is not used, there are no detection errors caused by distortion due to heating of the lens, and it is possible to obtain error free detection results.

In the above embodiment, two pinholes including a first pinhole 17 and second pinhole 19 are provided between the cell 11b and the photodiode photoreceptor 15, however, the present invention is not limited to this arrangement inasmuch as an unspecified plurality of pinholes may be provided.

In the present embodiment, two pinholes including a thirds pinhole 20 and fourth pinhole 24 are provided between the blue LED 14 and the cell 11b, however, the present invention is not limited to this arrangement inasmuch as no pinholes, or one pinhole, or three or more pinholes also may be provided between the blue LED 14 and the cell 11b.

In the present embodiment, the shape of the pinholes is circular, however, the present invention is not limited to this arrangement inasmuch as the shape of the pinholes may be elliptical, or polygonal such as triangular, or square and the like.

Although the turbidity detection apparatus (nucleic acid detection device) has been described as a device provided with a turbidity detection optical device in the above embodiment, the turbidity detection optical device may be is a device which eliminates scattered light from opaque material, and detects only the amount of light actually transmitted through that material, and as such may also be used in colorimetric analysis of opaque materials, colorimetric analyzers capable of optical absorbance analysis, and optical absorbance analyzers.

In the embodiment, a nucleic acid detection device is described as an example of a turbidity detection device, however, the present invention is not limited to this example inasmuch as other devices using turbidity detection, for example blood coagulation measurement devices, immunity measuring devices and the like also may be used.

In the embodiment, the nucleic acid detection device 30 is connected to the assay unit 31, and data processing unit 32 through a communication line, however, the present invention is not limited to this arrangement inasmuch as the nucleic acid detection device also may be integratedly formed with the assay unit 31 and data processing unit 32. Although the data processing unit 32 executes the detection cell 7 installation detection process, pipette chip 45 insertion detection process, and turbidity detection process in the above embodiment, part or all of these processes may be executed by the controller 41 provided in the assay unit 31, or executed by the processor, that is, CPU, of each turbidity detection optical device, or executed individually by the processor of each turbidity detection optical device 1.

The embodiment described above is a single embodiment, which may be variously modified insofar as such modification does not depart from the scope of the present invention, and is not limited to the embodiment described in the description.

What is claimed is:

1. An optical device comprising:
   a photoemitter for emitting light;
   a mounting unit for installing a transparent container accommodating a sample to be subjected to detection;
   a photoreceptor for receiving the light emitted by a photoemitter and transmitted through the transparent container installed in the mounting unit;
   a first member disposed between the transparent container and the photoreceptor, and having a first pinhole through which passes the light transmitted through the transparent container; and
   a second member disposed between the first member and the photoreceptor, and having a second pinhole through which passes the transmitted light that has passed through the first pinhole;
     wherein the optical device does not have a lens in the optical path from the photoemitter to the photoreceptor.

2. The optical device of claim 1, wherein the size of the second pinhole is smaller than the size of the first pinhole.

3. The optical device of claim 1 further comprising a third member disposed between the light source and the transparent container, and having third pinhole;
   wherein the light emitted from the photoemitter passes through the third pinhole and reaches the transparent container.

4. The optical device of claim 3, wherein the first pinhole, second pinhole, and third pinhole are provided in a straight line.

5. The optical device of claim 3 further comprising a fourth member disposed between the photoemitter and the third pinhole, and having a fourth pinhole;
   wherein the light emitted from the photoemitter passes through the fourth pinhole and third pinhole and reaches the transparent container.

6. The optical device of claim 1, wherein the photoemitter has an LED, and the photoreceptor has a photodiode.

7. The optical device of claim 6, wherein the LED is a blue color LED.

8. The optical device of claim 1 further comprising a heater for heating the transparent container installed in the mounting unit.

9. An optical device comprising:
   a photoemitter for emitting light;
   a mounting unit for installing a transparent container accommodating a sample to be subjected to detection;
   a photoreceptor for receiving the light emitted by a photoemitter and transmitted through the transparent container installed in the mounting unit;
   a first member disposed between the photoemitter and the transparent container, and having a first pinhole; and
   a second member disposed between the first member and the transparent container, and having a second pinhole through which passes the light transmitted through the first pinhole;

wherein the optical device does not have a lens in the optical path from the photoemitter to the photoreceptor.

10. The optical device of claim 9 further comprising a third member disposed between the transparent container and the photoreceptor, and having a third pinhole through which passes the light transmitted through the transparent container.

11. A turbidity detection apparatus comprising:
an optical device comprising:
a photoemitter for emitting light;
a mounting unit for installing a transparent container accommodating a sample to be subjected to turbidity detection;
a photoreceptor for receiving the light emitted by a photoemitter and transmitted through the transparent container installed in the mounting unit;
a first member disposed between the transparent container and the photoreceptor, and having a first pinhole through which passes the light transmitted through the transparent container; and
a second member disposed between the first member and the photoreceptor, and having a second pinhole through which passes the transmitted light that has passed through the first pinhole;
wherein the optical device does not have a lens in the optical
path from the photoemitter to the photoreceptor;
a heater for heating a sample accommodated in the transparent container installed in the mounting unit; and
a turbidity detection unit for detecting the turbidity of the heated sample accommodated in the transparent container based on the amount of light received by the photoreceptor.

12. The turbidity detection apparatus of claim 11 further comprising a mounting detection unit for detecting whether or not a transparent container is installed in the mounting unit based on the amount of light received by the photoreceptor.

13. The turbidity detection apparatus of claim 11, wherein the size of the second pinhole is smaller than the size of the first pinhole.

14. The turbidity detection apparatus of claim 11 further comprising a third member disposed between the photoemitter and the transparent container, and having a third pinhole;
wherein the light emitted from the photoemitter passes through the third pinhole and reaches the transparent container.

15. The turbidity detection apparatus of claim 14, wherein the first pinhole, second pinhole, and third pinhole are provided in a straight line.

16. The turbidity detection apparatus of claim 14 further comprising a fourth member disposed between the photoemitter and the third pinhole, and having a fourth pinhole;
wherein the light emitted from the photoemitter passes through the fourth pinhole and third pinhole and reaches the transparent container.

17. The turbidity detection apparatus of claim 11, wherein the photoemitter has an LED, and the photoreceptor has a photodiode.

18. The turbidity detection apparatus of claim 11, wherein the LED is a blue color LED.

19. The turbidity detection apparatus of claim 11, further comprising a data processing unit for obtaining a concentration of a marker gene contained in the sample based on the detected turbidity.

20. A turbidity detection apparatus comprising:
a photoemitter for emitting light;
a mounting unit for installing a transparent container accommodating a sample to be subjected to turbidity detection;
a photoreceptor for receiving the light emitted by a photoemitter and transmitted through the transparent container installed in the mounting unit;
a first member disposed between the transparent container and the photoreceptor, and having a first pinhole through which passes the light transmitted through the transparent container;
a second member disposed between the first member and the photoreceptor, and having a second pinhole through which passes the transmitted light that has passed through the first pinhole;
a turbidity detection unit for detecting the turbidity of a sample subjected to turbidity detection and accommodated in the transparent container based on the amount of light received by the photoreceptor;
an insertion unit for inserting a chip for supplying a sample to be subjected to turbidity detection in the transparent container; and
an insertion detection unit for detecting whether or not a chip is inserted in the transparent container installed in the mounting unit based on the amount of light received by the photoreceptor.

* * * * *